US008785174B2

(12) United States Patent
Ruiz

(10) Patent No.: US 8,785,174 B2
(45) Date of Patent: Jul. 22, 2014

(54) HEAVY METAL REMEDIATION SYSTEM

(75) Inventor: Oscar N. Ruiz, Toa Alta, PR (US)

(73) Assignee: Inter American University of Puerto Rico, San Juan, PR (US)

(*) Notice: Subject to any disclaimer, the term of this patent is extended or adjusted under 35 U.S.C. 154(b) by 491 days.

(21) Appl. No.: 12/859,590

(22) Filed: Aug. 19, 2010

(65) Prior Publication Data

US 2011/0220570 A1    Sep. 15, 2011

Related U.S. Application Data

(60) Provisional application No. 61/235,624, filed on Aug. 20, 2009.

(51) Int. Cl.
| *C12N 1/21* | (2006.01) |
| *C07H 21/02* | (2006.01) |
| *C12Q 1/34* | (2006.01) |
| *C02F 3/34* | (2006.01) |
| *C12N 15/70* | (2006.01) |
| *G01N 33/84* | (2006.01) |
| *C12N 1/20* | (2006.01) |
| *G01N 33/52* | (2006.01) |
| *C02F 101/20* | (2006.01) |

(52) U.S. Cl.
CPC *C12N 15/70* (2013.01); *C12Q 1/34* (2013.01); *C02F 3/341* (2013.01); *G01N 33/84* (2013.01); *C12N 1/20* (2013.01); *G01N 33/523* (2013.01); *C02F 2101/20* (2013.01)
USPC ..................................... 435/252.3; 536/23.1

(58) Field of Classification Search
None
See application file for complete search history.

(56) References Cited

U.S. PATENT DOCUMENTS

2006/0121604 A1* 6/2006 Handa et al. ................ 435/320.1
2010/0276373 A1* 11/2010 Acey et al. ..................... 210/679

OTHER PUBLICATIONS

Srivastava et al. Novel biofiltration methods for the treatment of heavy metals from industrial wastewater. J Hazard Mater. Feb. 28, 2008;151(1):1-8. Epub Sep. 29, 2007.*
Zhao et al. Simultaneous mercury bioaccumulation and cell propagation by genetically engineered *Escherichia coli*. Process Biochemistry 40: 1161-1616, 2005.*
Cursino et al. Mercury concentration in the sediment at different gold prospecting sites along the Carmo stream, Minas Gerais, Brazil, and frequency of resistant bacteria in the respective aquatic communities. Hydrobiologia 394: 5-12, 1999.*
Cols et al. Secretion of mouse-metallothionein by engineered *E. coli* cells in metal-enriched culture media.J Mol Microbiol Biotechnol. Oct. 2001;3(4):507-12.*
Babai et al. An *Escherichia coli* gene responsive to heavy metals. FEMS Microbiol Lett. Oct. 15, 1998;167(2):107-11.*
Sriraman et al. Transcription from heterologous rRNA operon promoters in chloroplasts reveals requirement for specific activating factors. Plant Physiol. Aug. 1998;117(4):1495-9.*
Olins et al. A novel sequence element derived from bacteriophage T7 mRNA acts as an enhancer of translation of the lacZ gene in *Escherichia coli*. J Biol Chem. Oct. 15, 1989;264(29)16973-6.*
Hayes et al. Sequence elements critical for efficient RNA editing of a tobacco chloroplast transcript in vivo and in vitro. Nucleic Acids Res. Aug. 7, 2006;34(13):3742-54.*
O'Farrell et al. Regulated expression by readthrough translation from a plasmid-encoded beta-galactosidase. J Bacteriol. May 1978;134(2):645-54.*
Zhang et al. A polyphosphate kinase (PPK2) widely conserved in bacteria. Proc Natl Acad Sci U S A. Dec. 24, 2002;99(26):16678-83. Epub Dec. 16, 2002.*
Farran I. et al., High-density seedling expressionsystem for the production of . . . in transgenic tobacco chloroplasts, Plant Biotech. J., 2008, v6, pp. 516-527.
Li, J. et al., Effect of metallothionein on cell viability and its interactions cadmium and zinc in HEK293 cells, Cell Biol. Int., 2005, v 29, pp. 843-848.
Iszard, M. B. et al., Characterization of metallothionein-1 in transgenic mice, Toxicol. Appl Pharmacol., 1995, v133, pp. 305-312.
Pan-Hou, H. et al., Evaluation of ppk-specific polyphosphate as a mercury remedial tool, Bio. Pharma. Bull., 2001, v 24, pp. 1423-1426.
Pan-Hou, H. et al., Polyphosphate produced in recombinant *Escherichia coli* confers mercury resistance, FEMS Microbiol. Lett., 2002, v207, pp. 159-164.
Khalil, H. E. et al., Heavy metal contamination from mining sites in south Morocco: monitoring metal content and toxicity of soil runoff and ground water, Environ. Monit. Assess., 2008, v 136, pp. 147-160.
Process Biochemistry, Zhao X, W. et al., Simultenious mercury bioaccumulation and cell propagation by genetically engineered *E. coli*, 40:1611-1616 (2005).
The Enzymes, Wallenfels K. et al., Beta Galactosidase, 7:617-663 (1972).
Biol. Pharma. Bull., Nagata T. et al., Accumulation of mercury in transgenic tobacco expressing bacterial polyphosphate, 29:2350-2353 (2006).
Biotechnol. Prog., Wen_Chen Kao et al., Localization effect on the Metal biosorption capability of recombinant mammal and fish metallothioneins in *Eschericia coli*, 22:1256-1264 (2006).
Applied and Environ. Microbiol., Shaolin Chen and David Wilson, Construction and characterization of *Eschericia coli* Genetically Engineered for bioremediation of mercury contaminated environments, 63:2442-2445 (1997).
Applied and Environ. Microbiol., Pazirandeh et al., Development of bacterium-based heavy metal biosorbents: enhanced uptake of cadmium and mercury by *Eschericia coli* expressing a metal binding motif, 64:4068-4072 (1998).
Biotechnology and bioengineering, Keasling, J.D. et al., Engineering polyphosphate metabolism in *Eschericia coli*: implications for bioremediation of inorganic contaminants, 58:231-239 (1998).
Biotechniques, Wilson Lynne et al., Bacterial-based heasvy metal biosorbents: enchanced uptake of cadmium by *E. coli* Expressing a metallothionein fused to B-galactosidase, 32:551-558 (2002).
Costantino Vetriani et al., Mercury Adaptation Among Bacteria From a Deep-Sea Hydrothermal Vent, Appl. and Envir. Microb. 71(1):220-226 (2005).

* cited by examiner

*Primary Examiner* — Michele K Joike
(74) *Attorney, Agent, or Firm* — Dr. Michael David, Esq.; Capitol City Techlaw PLLC

(57) ABSTRACT

The invention provides a system of heavy metal sequestration by bacteria. The bacteria expresses the ppk, mt, and/or β-galactosidase (lacZ) genes and can tolerate at least 25 μM mercury, 1,000 μM zinc, 250 μM cadmium, and 3,000 μM Pb. The system allows for facile determination of the presence of heavy metal contaminants in a liquid and the facile collection of the bacteria that has sequestered large amounts of heavy metal. Further provided is a system of gene expression in bacteria that comprises phage and plastid gene expression elements and delivers a particularly high level of protein expression and heavy metal resistance.

18 Claims, 14 Drawing Sheets
(6 of 14 Drawing Sheet(s) Filed in Color)

pBSK-Prrn-5'UTR-*lacZ*-3'UTR
at 120 μM Hg
pBSK-Prrn-5'UTR-*mt-1*-3'UTR
at 120 μM Hg
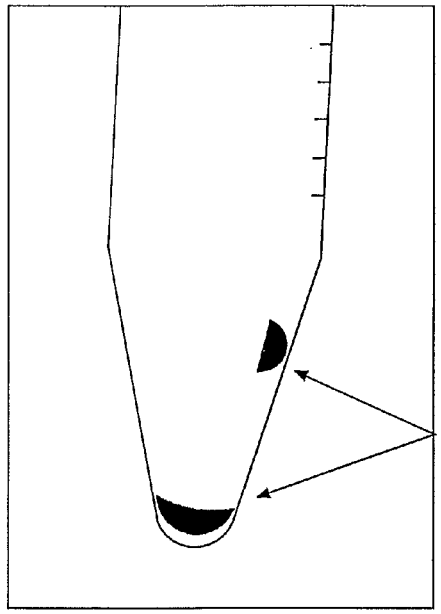
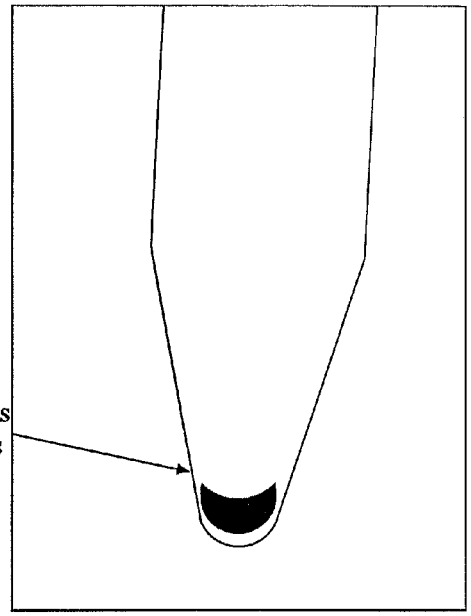
Solid Aggregates and Precipitates
Figure 6A
Figure 6B

HEAVY METAL REMEDIATION SYSTEM

This patent application claims priority from U.S. Provisional Patent Application No. 61/235,624, filed Aug. 20, 2009.

This invention was made in part with materials developed under U.S. government grant NSF CBET-0755649 awarded by the National Science Foundation. The government may have certain rights in the invention.

BACKGROUND OF THE INVENTION

1. Field of the Invention

This invention relates to the field of molecular biology to create genetically modified bacteria resistant to and capable of sequestering and accumulating heavy metals, including mercury, lead, zinc, and cadmium, for bioremediation of contaminated liquids and solids.

2. Description of the Background

Metallic chemical elements that have a relatively high density are often referred to as heavy metals. The heavy metals are toxic even at low concentrations. Toxic heavy metals include mercury, cadmium, lead, zinc and silver. Among the heavy metals, mercury, lead, and cadmium are considered particularly toxic.

Mercury has been introduced into the environment as a byproduct of industrial and natural processes and can accumulate in soil and sediments in high concentrations. Patra, M. and Sharma A., Bot. Rev. 66:379-422 (2000). In the United States, coal burning power plants emit about 48 tons of mercury annually, while in Asia and Africa coal burning power plants release more than 1500 tons per year. Clean Air Mercury Rule. U.S. Environmental Protection Agency ("EPA") 2009, Retrieved Feb. 8, 2009 from the U.S. Environmental Protection Agency website. Globally the annual mercury emissions from all sources are estimated at 4800-8300 tons. Mercury Human Exposure, EPA 2008, Retrieved Feb. 8, 2009 from the U.S. Environmental Protection Agency website.

Mercury compounds are neurotoxins and potent blockers of electron transport in the cell. All mercury forms are toxic and present risks to human health and to the environment. Developing a cost-efficient and effective remediation system is of utmost importance.

Current remediation strategies to clean mercury from the environment include flushing, chemical reduction/oxidation, excavation, retrieval and off-site disposal. These approaches are expensive, environmentally disruptive, and inefficient. Karenlampi, S. et al., Environ. Pollut. 1007:225-231 (2000). Other methods, such as vitrification and concrete capping, render the site unusable and are impractical in remediation of large areas. The cost of remediating a pound of mercury from the environment with current technologies is in the several thousands of dollars. Hussein, H. et al., Env. Sci. Technol. 41:8439-8446 (2007).

Like mercury, other heavy metals, such as lead and cadmium, present a serious environmental threat and must be remediated. Lead is a powerful neurotoxin that can accumulate in soft tissue and bones. Because of its toxicity lead has been banned by the EPA and other Agencies from consumer products including paints, gasoline, water pipes, toys, and others. The EPA limits lead content to less than 0.015 ppm in drinking water. Lead ranks second in the 2007 Comprehensive Environmental Response Compensation, and Liability Act (CERCLA) priority list of hazardous substances.

The current wide spread use of cadmium in multiple consumer applications, especially in batteries, has increased environmental pollution of this heavy metal. Cadmium has been shown to be highly toxic, causing serious poisoning, bone degeneration, cellular enzymes inhibition, and cell membrane disruption. As in the case of mercury, current methods to remediate or capture lead and cadmium rely on the use of physicochemical methods including the use of ion exchange resins, precipitation and extraction, burial, site capping, and offsite disposal. Kim, S. et al. J. Biosci. Bioeng. 99:109-114 (2005). These methods are costly and/or disruptive to the environment being reclaimed. New technologies are required to facilitate the remediation of contaminated environments.

Bioremediation, the use of organisms for the restoration of contaminated environments, may present a potentially low cost and environmentally friendly approach. For example, bacteria can break down certain toxic compounds into their non-toxic metabolites. However, heavy metal elements, such as mercury, cadmium and lead, can not be detoxified into non-toxic metabolites.

A method of mercury bioremediation, by volatilization of mercury, relies on the expression of the mer operon, which manages the transport and reduction of $Hg^{2+}$. One of the mer operon genes, merA, codes for mercuric ion reductase, an enzyme that catalyzes the conversion of $Hg^{2+}$ to $Hg^0$. $Hg^0$ is a less volatile, less-reactive and less toxic form of mercury. Jackson, W. J. and Summers, A. O., J. Bacteriol. 151:962-970 (1982). In the volatilization process, however, elemental mercury is released into the environment where it can be converted into more toxic forms. Another disadvantage to the volatilization method is that it is not suitable for water treatment, because bacteria release the volatilized elemental mercury into the same water that is being remediated.

Bacteria do not have endogenous mechanisms that provide high resistance to mercury, while allowing mercury accumulation inside the cell. Genetic engineering has been used to integrate genes from other organisms with the goal of increasing mercury resistance and accumulation. Molecules known as chelators or sequestration agents have been proposed as suitable heavy metal scavenging agents that can be expressed in organisms with the goal of recovering the heavy metals from soil or water.

Metallothionein and polyphosphate in bacterial systems have been implied in the detoxification of some heavy metals. These two agents, expressed in *E. coli*, can sequester mercury, cadmium and lead and thus protect the bacteria from certain levels of these heavy metal elements. The results to date, however, have been discouraging. The bacteria can not effectively sequester these elements and do not survive high levels of these heavy metals. These results are attributed to a perceived lack of stability of the chelator protein agent, creating bacterial systems with weak tolerance for the heavy metal.

Metallothioneins are encoded by the mt genes found in mammals, plants, and fungi. Sousa, C. et al., J. Bacteriol. 180:2280-2284 (1998). Metallothionein (MT), however, has been shown to be unstable when expressed in bacteria. Berka, T. et al., J. Bacteriol. 170:21-26 (1988). Because the MT protein was found to be unstable when expressed in bacteria, the mt gene has been fused with stabilizing agents such as glutathione-5-transferase (GST) creating GST-MT fusions. Chen, S. and Wilson D. B., Appl. Env. Microbiol. 63:2442-2445 (1997). Various GST-MT constructs included *S. cerevisiae* (GST-YMT), human (GST-HMT) and pea (GST-PMT). Cells harboring GST-HMT have not been shown to produce soluble MT proteins and the construct does not confer any resistance to mercury. Cells expressing the YMT and PMT constructs have been shown to tolerate liquids having at most 5 µM mercury, a level that is barely toxic. More importantly, cells expressing these two constructs do not appear to accumulate mercury or protect the cell from mercury, unless the cell is further engineered to express mercury transport genes of the mer operon. Various unsuccessful attempts have also been made to engineer multiple copies of mt gene of *N. crassa* and other human mt genes, targeted to the bacterial periplasm. The instability and insolubility of these proteins, however, have continued to prevent their use as effective remediation agents. Valls, M. and Lorenzo, V., FEMS Micro. Reviews, 26:327-338 (2002). Although these fusions proteins confer some limited tolerance to mercury, this effect can not be clearly attributed to the MT proteins because GST, the fusion partner, is also known to bind heavy metals such as mercury. Chen, S. and Wilson D. B., Appl. Environ. Microbiol. 63:2442-2445 (1997); Deng, X. and Wilson D. B., Appl. Microbiol. Biotechnol. 56:276-279 (2001); Custodio, H. M., et al., Arch. Environ. Occup. Health 60:17-23 (2005).

Therefore, it has been concluded that the transgenic bacteria modified with metallothionein genes have not provided adequate resistance in cells. Beattie, J. H. et al., Toxicol. Lett. 157:69-78 (2005); Odawara, F. et al., J. Biochem. 118:1131-1137 (1995); Park, J. D., et al., Toxicology. 163:93-100 (2001). Explanations given for this failure include rapid degradation of the small metallothionein peptide by cellular proteases, low protein yield, and possible interference with redox pathways in the cytosol. Sousa, C. et al., J. Bacteriol. 180:2280-2284 (1998); Yang, F. et al., Protein Expr. Purif. 53:186-194 (2007).

Also, attempts to engineer bacteria with metallothionein genes to enhance resistance to zinc have proven ineffective. Odawara, F. et. al., supra.

Metallothionein fusion genes expressed in bacteria have shown to provide but marginal tolerance to cadmium toxicity to up to 50 mg/liter (about 150 µM). Odawara, F. et. al., Id.; Keasling, J. D., and Hupf, G. A. Applied Env. Microbiol. 62:743-746 (1996). These studies do not indicate that bacteria can grow well in high cadmium concentrations because after 50 mg/L of cadmium the transgenic cell had a substantial decrease in growth in comparison with transgenic cells growing in media without cadmium.

Others have focused on engineering the polyphosphate kinase ("ppk") gene for expression in bacteria. The ppk enzyme is responsible for the synthesis of long linear polymers of orthophosphates known to absorb (sequester) mercury. Similarly to mt, only ppk fusion constructs have been proposed and utilized. For example, the *Klebsiella aerogenes* ppk gene has been fused with *Pseudomonas* derived merT and merP genes. The merT and merP genes facilitate internalization of mercury. The fusion was meant to improve stability and the fusion components were chosen in part due to the belief that mercury internalization would be limited, which would also limit the bioremediation effect of the bacteria expressing the ppk gene. Pan-Hou, H. et al., Biol. Pharm. Bull. 24:1423-1426 (2001); Pan-Hou, H. et al., FEMS Microbiol. Lett. 10325:159-164 (2002). Bacteria expressing these constructs are capable of accumulating up to 16 µM mercury and 24 µM of an organo-mercury compound from solutions. Bacterial growth in the presence of elemental mercury was abolished at 16 µM mercury. Increased resistance to mercury has been shown when the engineered bacteria expressing the constructs were placed on alginate beads. Nevertheless, mercury remediation is inactivated and the bacteria loses viability in the presence of 40-80 µM mercury. Kyono, M. et al., Appl. Microbiol. Biotechnol. 62:274-278 (2003).

Phytoremediation and mycoremediation (non-engineered organisms) have been the methods used to attempt to bioremediate lead, by accumulating lead in the roots or leaf. Huang, L. Z. et al., Biodegradation 20:651-660 (2009); Vimala, R. and Das, N., J., Hazard. Mat. 168:376-382 (2009). No effective bacterial bioremediation technology has been proposed for lead as of today.

The low level of resistance of the engineered bacteria to the heavy metal achieved by the above mentioned systems preclude their application as an effective bioremediation system. Even in water with low mercury concentrations, these systems would not be effective because mercury will accumulate in the cell to concentrations higher than what is tolerated by the system.

SUMMARY OF THE INVENTION

In one aspect of the invention, the invention provides a vector for expression of a heavy metal chelating gene in a bacterium, comprising functionally connected elements:
a vector backbone,
a transcriptional constitutive promoter sequence derived from the plastid 16S rrn gene,
a translational enhancer element sequence derived from bacteriophage T7 gene 10,
a coding sequence of a chelator agent,
wherein the vector is in the bacterium. In a preferred embodiment, the vector further comprises a 3'UTR Rho-independent translational terminator. Preferably, the 3'UTR is the plastid rps16 transcriptional terminator or the *E. coli* rrnB transcriptional terminator. More preferably, the 3'UTR is the plastid rps16 transcriptional terminator.

In another embodiment, the chelator agent is encoded by a mt, a ppk, or a β-galactosidase (lacZ) gene and the gene is expressed in a bacterium. In accordance to one embodiment, the chelator agent are polyphosphates synthesized by ppk and the bacterium is resistant to up to about 100 µM mercury, at least about 1000 µM zinc, at least about 250 µM cadmium or at least about 3,000 µM lead.

In yet another embodiment the mt gene is a mammalian metallothionein. More preferably the chelator agent is encoded by a mouse mt1 gene sequence and the bacterium is resistant to up to about 160 µM mercury, at least 250 µM cadmium, 1,000 µM zinc or 3,000 µM lead.

In still another embodiment, the chelator agent is encoded by a β-galactosidase (lacZ) gene sequence and the bacterium is resistant to up to about 140 µM mercury and at least 250 µM cadmium, 1,000 µM zinc or 3,000 µM lead.

In a further still another embodiment, the vector backbone is a plasmid backbone.

In another aspect, the invention provides a bacterium comprising a transgenic chelator agent, wherein the bacterium is resistant to between at least about 25 µM and at least about 100 µM Hg. In a preferred embodiment, the chelator agent gene is transcribed from a strong promoter, flanked by select 5' UTR, and optionally, 3'UTR, such as at least between 4,000 and 8,500 copies of stable transcripts per ng total mRNA correspond to the chelator gene, more preferably between 6,000 and 7,500 copies of stable transcripts per ng total mRNA correspond to the chelator gene. In yet more preferred embodiments, the chelator agent gene is transcribed from a transcriptional constitutive promoter sequence derived from the plastid 16S rrn gene, the chelator agent gene is flanked by a 5' UTR translational enhancer element sequence derived from bacteriophage T7 gene 10. Yet still more preferably, the chelator agent gene is transcribed from a transcriptional constitutive promoter sequence derived from the plastid 16S rrn gene and is flanked by a 5' UTR translational enhancer element sequence derived from bacteriophage T7 gene 10 and a plastid rps16 gene 3'UTR Rho-independent translational terminator sequence.

In a preferred embodiment, the chelator sequestration agent coding sequence corresponds to the mt1 gene and the bacterium is resistant to up to about 160 μM mercury or to at least about 250 μM cadmium, 1,000 μM zinc or 3,000 μM lead. In another preferred embodiment, the sequestration agent coding sequence corresponds to a β-gal (β-galactosidase/lacZ) gene and the bacterium is resistant to up to about 140 μM mercury or to at least about 250 μM cadmium, 1,000 μM zinc or 3,000 μM lead. In still another preferred embodiment, the sequestration agent coding sequence corresponds to a β-gal gene and the bacterium is resistant to up to about 140 μM mercury or to at least about 1,000 μM zinc or 3,000 μM lead. In still yet another preferred embodiment, the sequestration agent coding sequence corresponds to a ppk gene and where the bacterium is resistant to about 250 μM cadmium, 1,000 μM zinc or 3,000 μM lead.

In a further embodiment, the bacterium comprises mt, ppk, or β-gal gene sequences, which are functionally connected to a transgene expression system further comprising:

a transcriptional constitutive promoter derived from a plastid 16S rrn gene, a translational enhancer element derived from bacteriophage T7 gene 10, and a Rho-independent transcription terminator sequence.

In a further still embodiment, the bacterium when in a liquid environment containing mercury, cadmium, zinc or lead, accumulates the mercury, cadmium, zinc or lead and turns dark in coloring in the presence of mercury.

In a yet further still embodiment, the bacterium when in a liquid environment containing mercury, cadmium, zinc or lead, accumulates the mercury, cadmium, zinc or lead and the bacterium forms aggregates and precipitates. In a different yet further still embodiment, the bacterium when in a liquid environment containing mercury, accumulates the mercury, and the bacterium forms aggregates and precipitates.

In accordance to one embodiment, the bacterium is an *E. coli, Pseudomonas, Cyanobacteria* or *Bacillus*.

In a different embodiment, when the bacterium comprising the mt, ppk, or β-gal gene sequences is grown on a biofilter, it can remove heavy metal from a contaminated liquid. And it is conveniently handled, e.g. removed from the liquid.

In another different embodiment, the ability of β-galactosidase to cleave 5-Bromo-4-chloro-3-indolyl-β-D-galactopyranoside (X-gal) is reduced by the presence of a heavy metal, proportionally in respect to the concentration of the heavy metal.

In another aspect, the invention provides a method to decontaminate mercury from a liquid, comprising:

adding a bacterial culture expressing a mt, ppk, or β-galactosidase gene to the liquid, wherein bacteria in the bacterial culture is resistant to between about 25 μM Hg and at least about 100 μM Hg, and removing the bacteria from the liquid after a period of time sufficient to allow sequestration of the mercury. In accordance to one embodiment of the method, the bacterium is removed after it creates clumps. In accordance to a preferred embodiment, the bacteria is removed by sieving, aspiration or removal of the bacteria from a filter.

In accordance to another aspect, a method to monitor mercury levels is provided, comprising adding a bacterial culture expressing β-galactosidase gene to the liquid, wherein bacteria in the bacterial culture is resistant to between about 25 μM Hg and at least about 140 μM Hg, and adding X-gal to a sample and testing the sample to determine the ability of the bacteria to metabolize 5-Bromo-4-chloro-3-indolyl-β-D-galactopyranoside (X-gal) to produce blue coloring in order to determine the concentration of mercury in the sample.

In another embodiment the invention provides a method to decontaminate mercury from a liquid, comprising placing the liquid in a device comprising a solid matrix, wherein said matrix further comprises β-galactosidase without a cellular carrier; and collecting the liquid as it is eluted from the solid matrix.

In another aspect, the invention provides a kit for detection of heavy metal contamination comprising:

a container for fluids, a bacterial culture expressing β-galactosidase or β-galactosidase enzyme on an indicator strip, X-gal, and a chart showing coloring corresponding to various concentrations of Hg in a liquid in contact with the bacterial culture expressing β-galactosidase or β-galactosidase enzyme on an indicator strip. In accordance to one embodiment, the kit further comprises a colorimetric enhancer.

In yet another aspect, the invention provides a kit for detection of heavy metal contamination comprising:

a container for fluids, a bacterial culture expressing β-galactosidase, ppk, or mt1, and an indicator strip showing dark coloring corresponding to the coloring of the bacterial culture expressing β-galactosidase, ppk, or mt1 when grown in the presence of various concentrations of the heavy metals in a liquid.

BRIEF DESCRIPTION OF THE DRAWINGS

The patent or application file contains at least one drawing executed in color. Copies of this patent or patent application publication with color drawing(s) will be provided by the United States Patent and Trademark Office upon request and payment of the necessary fee.

FIG. 1 illustrates the ability of bacteria to grow in the presence of the indicated concentrations of mercury. The cultures were grown in mercury for 16 hours before their growth was measured as a function of the optical density of the cultures ($OD_{600}$).

FIG. 2 illustrates the ability of bacteria to grow in the presence of the indicated concentrations of mercury. The cultures were grown in mercury for 120 hours and their growth was measured as a function of the optical density of the cultures. ($OD_{600}$).

FIG. 3 illustrates the transcriptional efficacy of constructs made in accordance to the invention. cDNA was prepared off the mRNA for the sequestration agent. The mRNA copy numbers were calculated and normalized to total RNA extracted.

FIG. 6 is a drawing representing aggregation of bacteria expressing the lacZ and mt1 genes grown in 120 μM mercury. The drawings of FIG. 6 are schematic representations of Polaroid pictures of observed aggregations. The precipitation was observed in cultures of bacteria engineered for expression of the lacZ gene (FIG. 6A) and mt1 gene (FIG. 6B).

FIG. 7 illustrates the ability of the bacteria engineered to express sequestration agents to remediate mercury contaminated media, i.e. to render the media harmless to bacteria that do not express the sequestration agents ("wt").

FIG. 9 demonstrates the reduction of β-galactosidase activity in bacteria expressing β-gal in accordance to the invention.

FIG. 10 shows bacterial bioassays that demonstrate the ability of bacterial cell lines comprising the pBSK-P16S-g10-lacZ-3'UTR ("lacZ"), pBSK-P16S-g10-mt1-3'UTR ("mt1"), and pBSK-P16S-g10-ppk-3'UTR ("ppk") expression cassette to tolerate and grow in media containing the indicated concentrations of cadmium, lead, and zinc. The untransformed $E.$ $coli$ strain JM109 was used as a control. Bacterial culture absorbance (OD 600 nm) was measured after 24 hrs growth in LB nutrient media supplemented with zinc, cadmium, and lead.

Figure 1A:
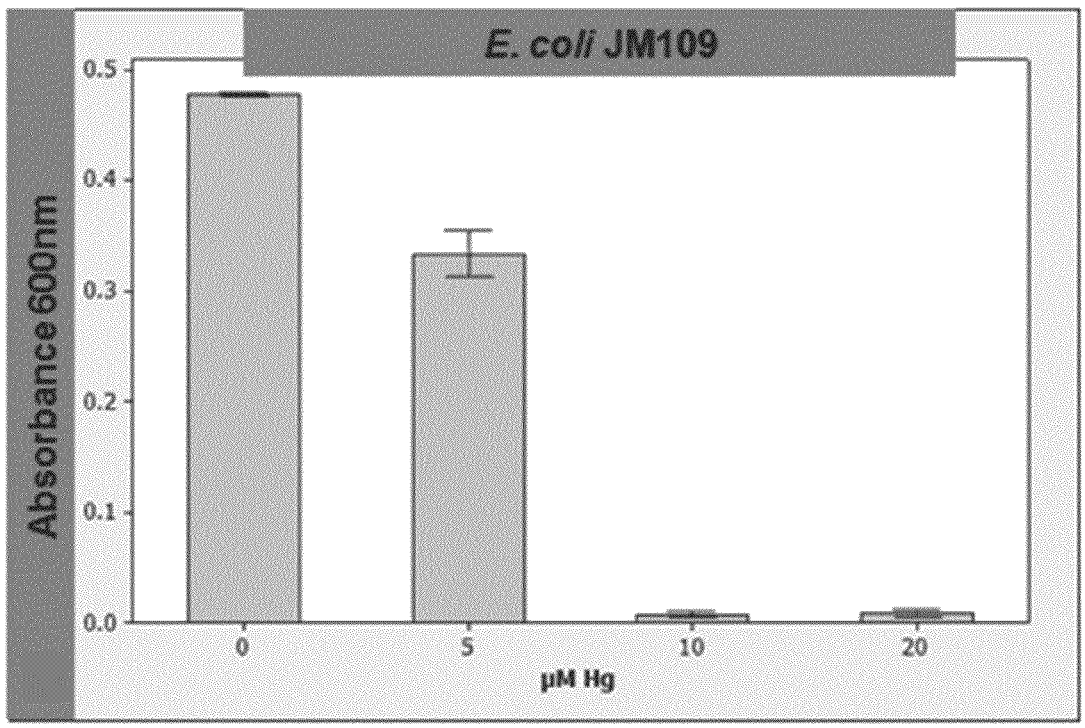
FIG. 1A represents untransformed bacteria.
Figure 1B:
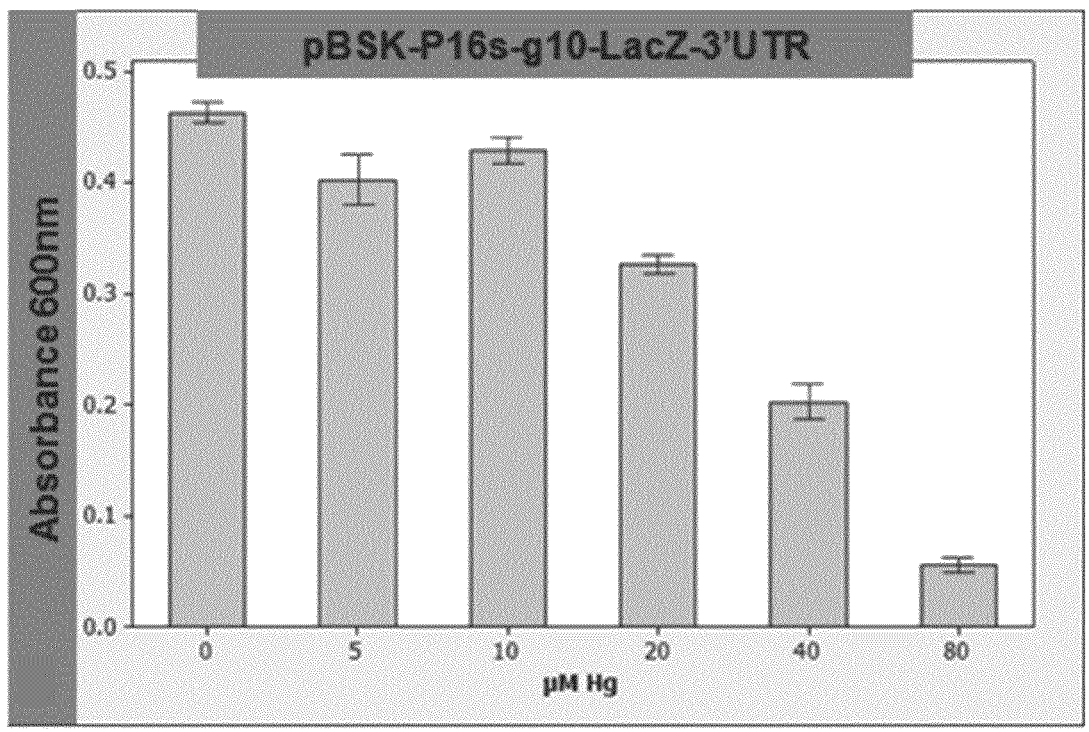
FIG. 1B represents engineered bacterial cultures, comprising the indicated plasmid expressing the β-gal protein.
Figure 1C:
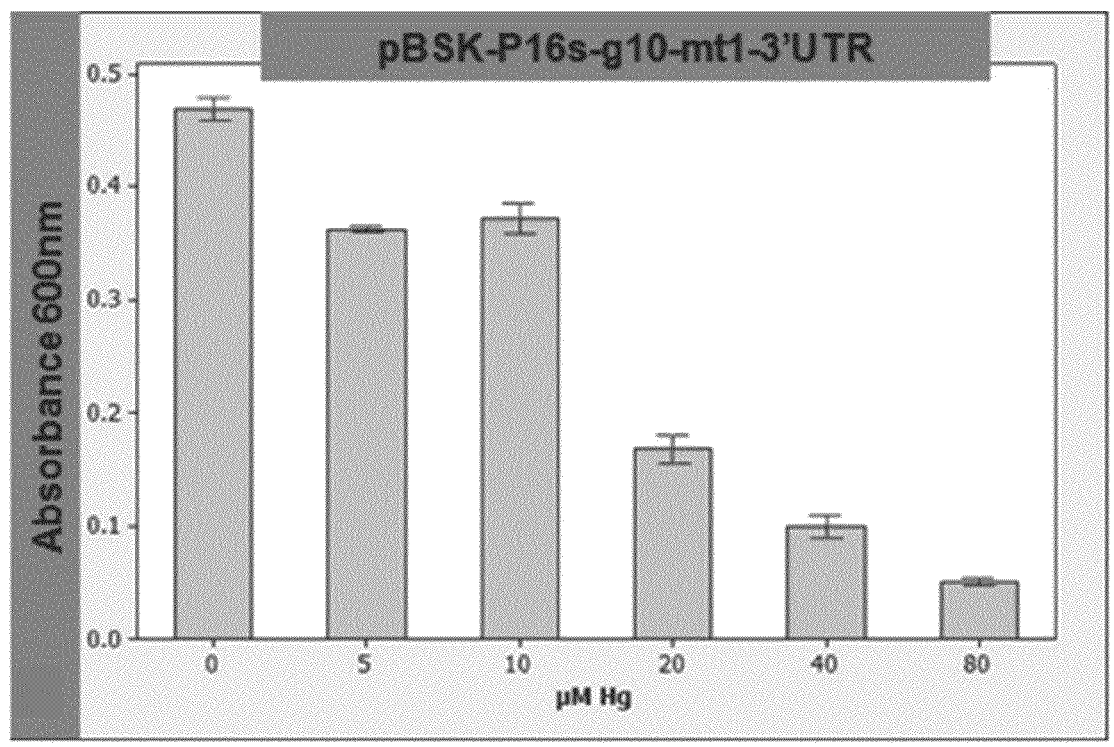
FIG. 1C represents engineered bacterial cultures, comprising the indicated plasmid expressing the mt1 protein.
Figure 1D:
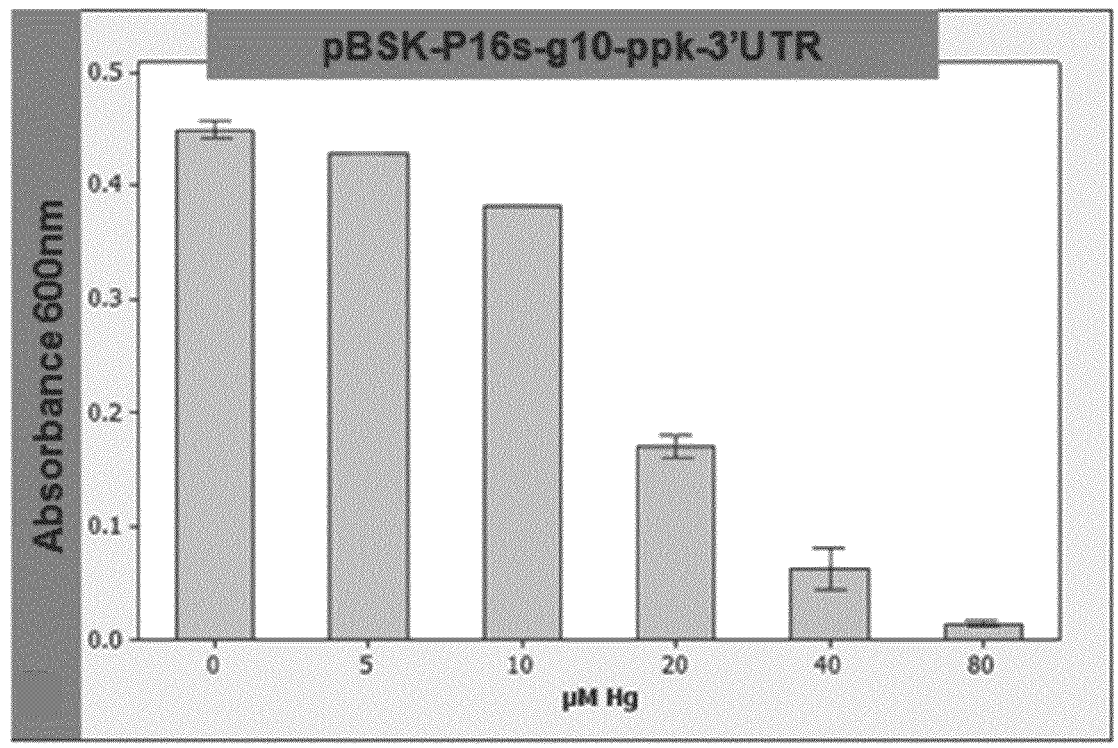
FIG. 1D represents engineered bacterial cultures, comprising the indicated plasmid expressing the ppk enzyme.
Figure 2A:
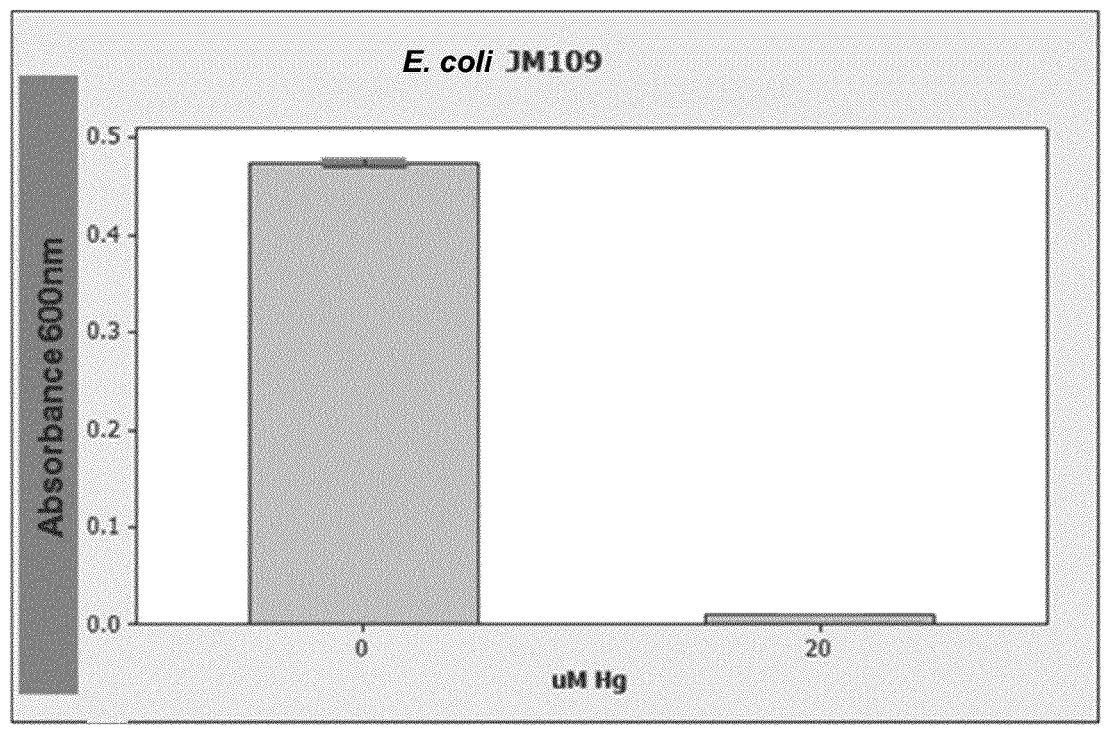
FIG. 2A represents untransformed bacteria.
Figure 2B:
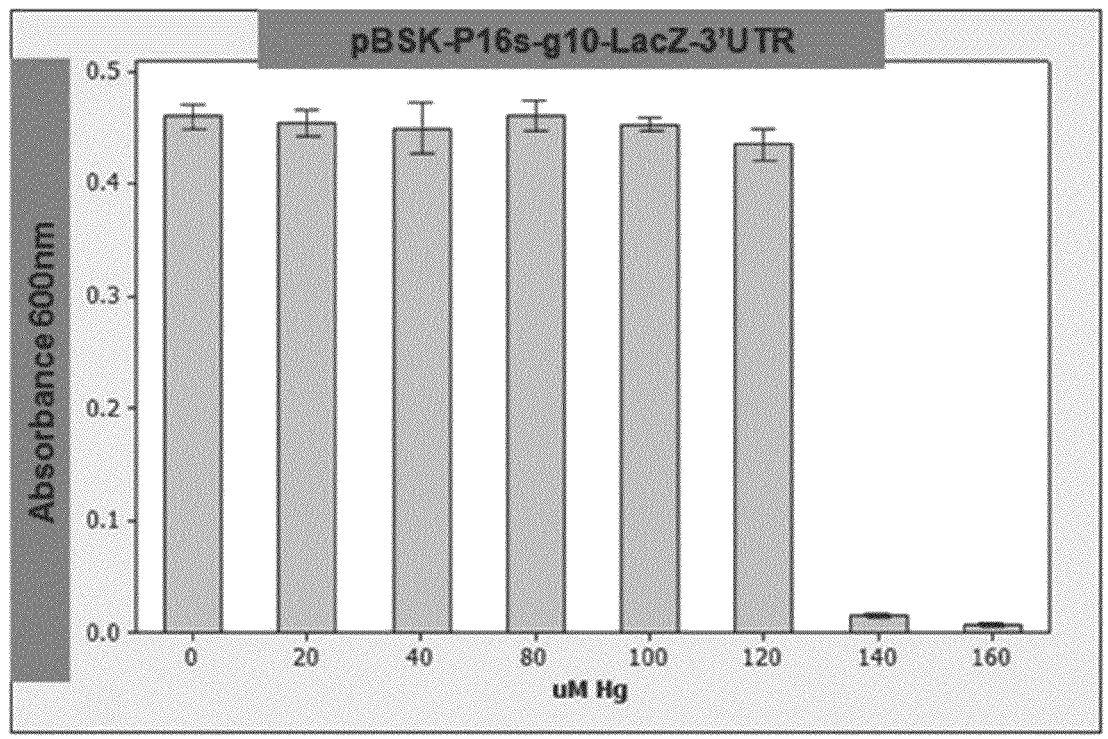
FIG. 2B represents engineered bacterial cultures expressing the β-gal protein.
Figure 2C:
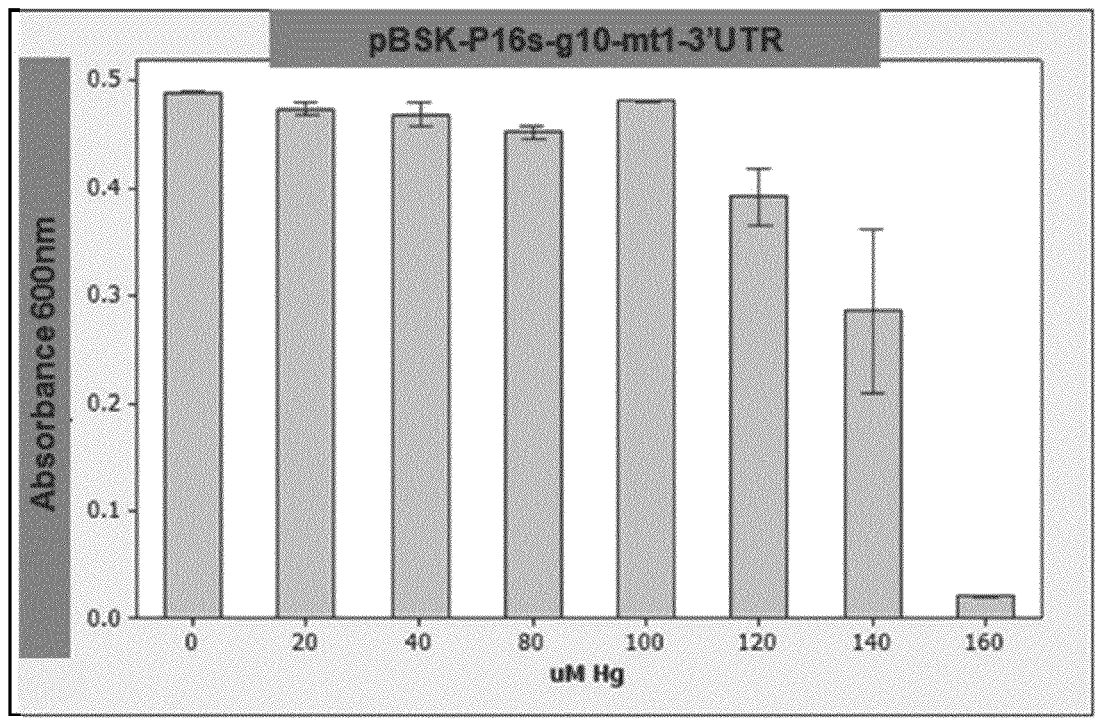
FIG. 2C represents engineered bacterial cultures expressing the mt1 protein.
Figure 2D:
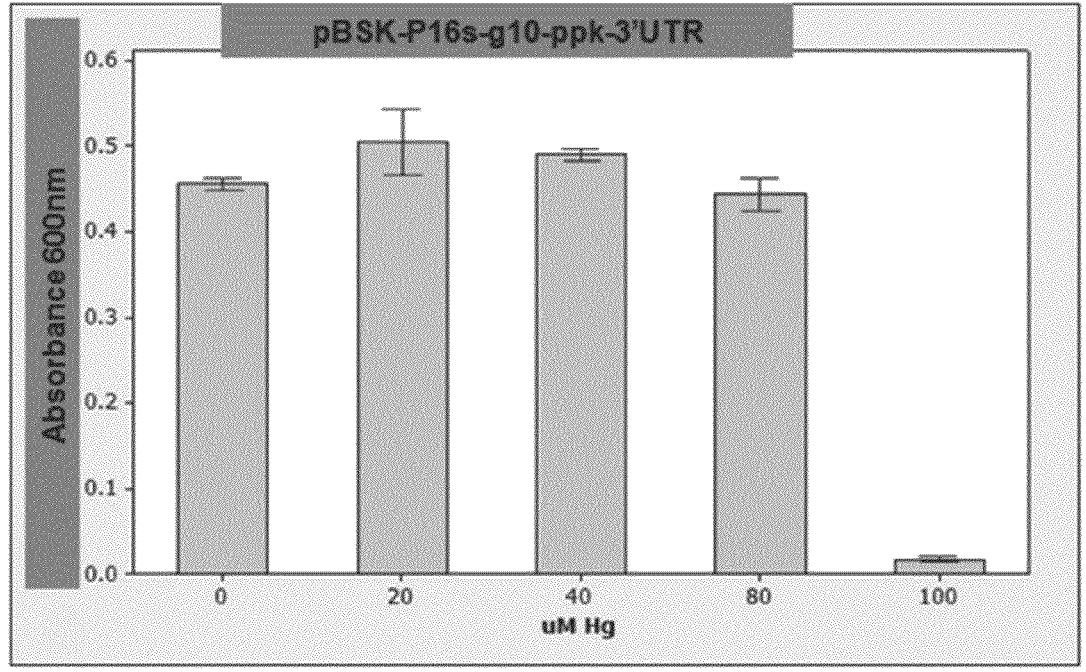
FIG. 2D represents engineered bacterial cultures expressing the ppk enzyme.
Figure 3A:
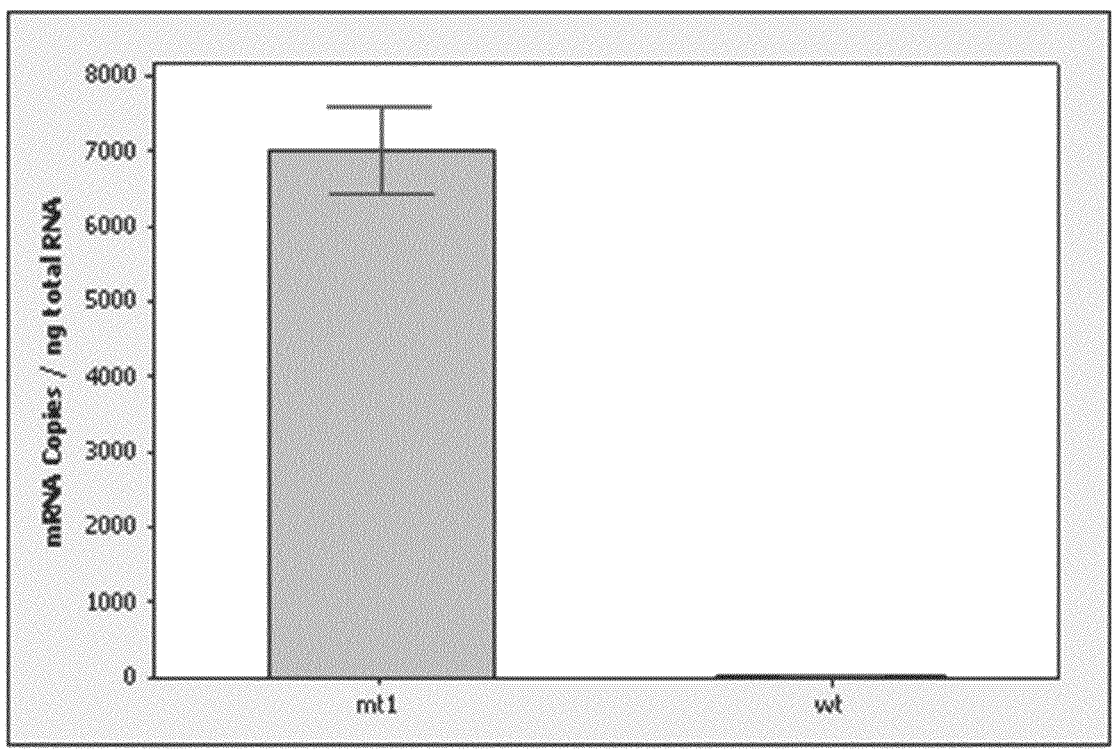
FIG. 3A compares cDNA produced in vitro from mRNA transcript in untransformed bacteria ("wt") and in bacteria transformed with the P16s-g10-mt1-3'UTR genetic construct.
Figure 3B:
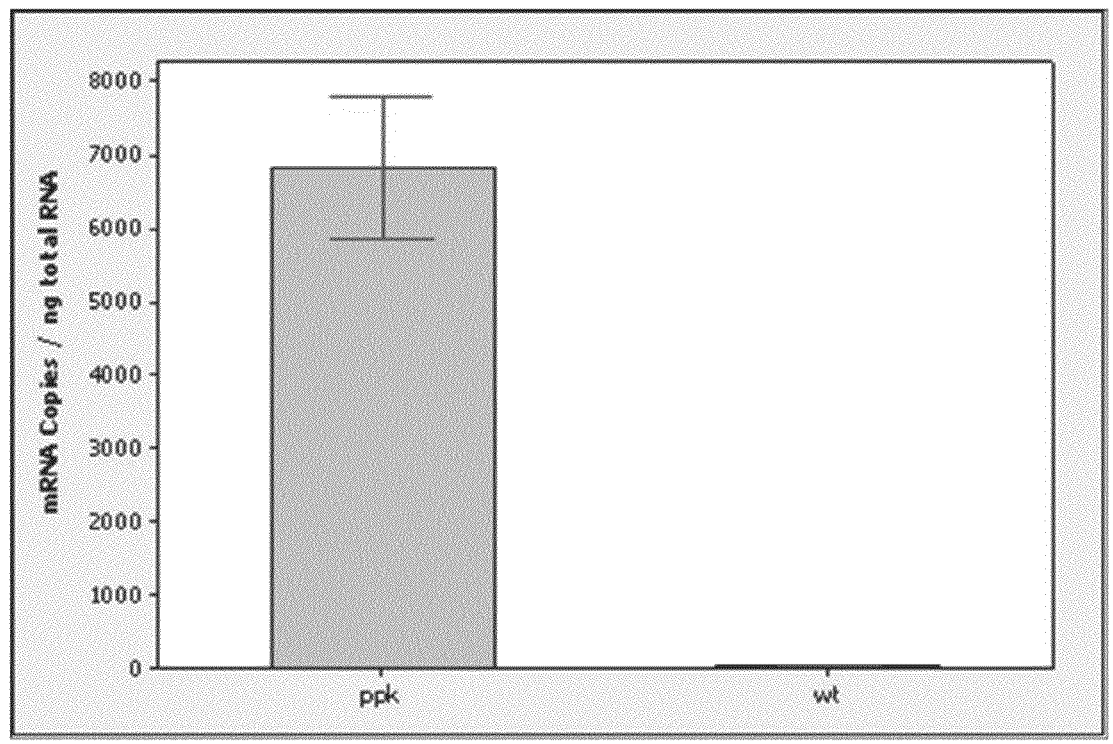
FIG. 3B compares cDNA produced in vitro from mRNA transcript in wt bacteria and in bacteria transformed with the P16s-g10-ppk-3'UTR genetic construct.

The experiments depicted in these Figures were performed multiple times. In experiments depicted in Figures showing bar deviations (FIGS. 1, 2, 3, 7, 10 and 11), the experiments were performed at least in triplicate and the bars show one standard deviation within the results.

Unless indicated otherwise, in the experiments depicted in these figures where bacterial growths are measured, the starting inoculum ("seed") for each culture was an equal sized aliquot of a starter culture at 0.01 $OD_{600}$.

In certain experiments testing the effectiveness of the lacZ construct, the bacterial cultures (untransformed and transformed) contained 200 mg/ml IPTG. However, it should be noted that in experiments where the lacZ gene is transcribed off a constitutive promoter, no induction of expression by IPTG was required.

DETAILED DESCRIPTION

The present invention provides a safe, efficient and cost-effective method for heavy metal remediation using chelation/sequestration agents. A preferred embodiment focuses on the use of bacterial cells expressing sequestration agents.

Three exemplary sequestration agents have been expressed in bacteria, rendering the bacteria resistant to high levels of heavy metal, and in particular to lead, cadmium, zinc and mercury: the metallothionein (mt), the polyphosphate kinase (ppk), and β-galactosidase proteins. Surprisingly, it has now been shown that sequestration agent genes can be expressed in bacteria in a manner that produces high levels of expression and resistance of the host cell to heavy metals. In accordance to another preferred embodiment, non-cell-based sequestration agents are employed.

In the bacterial cell based systems, the chelator agent protein is expressed without necessarily being part of a fusion protein. No concurrent expression of mer genes is required. No supporting beds of alginate or like compounds are required for the bacteria expressing these genes. The engineered cells withstand high levels of the heavy metals. These surprising observations have allowed the development of effective approaches to cellular and protein based bioremediation, as described in this application.

In one embodiment of the present invention, a vector is provided to introduce and express a gene in a host bacterial cell. The vector is a nucleic acid structure capable of replicating in a host bacterial cell. The vector backbone may include genes for transformation markers, to indicate transformation of the bacterial cell with the vector. A transformation marker may be a selective marker gene used to differentiate and select cells in which the vector is present from normal cells without the vector. Such markers are well known to artisans skilled in the art. Commonly used selective markers include genes that confer resistance to specific antibiotics, such as ampicillin. Some vector backbones may also include marker genes that merely indicate which cells were transformed with the vector. Transformation markers are well known to artisans skilled in the art. A commonly used indicator marker gene is the sequence of the lacZ gene encoding the β-galactosidase enzyme. Other commonly used transformation markers include various luciferase genes and GFP. The transformed bacteria remediates liquids or solid surfaces on which it grows. Alternatively, the solid surfaces are first bathed/leached of heavy metal by exposure to liquids and then the organism engineered in accordance to the invention removes the heavy metal from the liquid.

One component of the vector is a cloning site comprising multiple restriction enzyme recognition sequences, where these markers as well as additional desired nucleic acid sequences may be introduced into the vector and, by transformation, into the cell.

A preferred vector of the invention is a plasmid. A preferred plasmid is a plasmid engineered to allow the expression of transgenic genetic sequences. There are large numbers of vectors known and characterized. See, for example the Stanford University's vector database, on the Stanford University's website, last visited on Jun. 30, 2009. Examples of plasmids that allow for relatively facile introduction of expression cassettes are well-known in the art and are available commercially. A preferred vector is the pBlueScript®.

In one particular embodiment, a plasmid for the expression of chelating agents in a bacterial cell was provided. The plasmid comprised an expression cassette with a chelator gene and other elements that allow the plasmid to express the chelator gene in a bacterial cell to high levels. The other elements ("gene expression elements") included a promoter sequence, a translational enhancer sequence and a transcription termination sequence, all functionally connected in a manner well understood by an artisan skilled in the art. It should be noted that the chelator gene might be sufficiently expressed to levels described herein even absent a transcription termination sequence, although the presence of all three expression elements, selected for their ability to strongly enhance expression, is desirable.

Any effective combination of regulatory features might create a satisfactorily high and stable expression system. The invention is preferably practiced with a strong transcriptional promoter. It is contemplated that the plasmid may include different types of promoters, for example constitutive promoters, inducible promoters, cell specific or tissue specific promoters. Likewise, it is possible that other effective transcription enhancers and terminators may, in particular combinations, produce satisfactorily high and stable expression.

In one preferred embodiment, a constitutive promoter derived from the plastid 16S rrn gene sequence was utilized. Sriraman, P. et al., Plant Physiol. 117:1495-1499 (1998) and Yukawa, M. et al., Plant Molecular Biology 23:359-365 (2005). The 16S rrn promoter sequence was integrated as a functional element of the cassette.

Another element of the expression cassette provided in one embodiment of by the present invention is a translational enhancer sequence ("5' UTR"). The translational enhancer sequence enhances the translation of the transgenic protein sequence in the plasmid. A preferred translational enhancer in accordance with the invention was the bacteriophage T7 gene 10 5' enhancer element. Olins, P. O. and Rangwala, S. H., J. Biol. Chem. 264:16973-16976 (1989). The sequence of the enhancer element utilized in the invention was integrated in the expression cassette within the synthetic 5' gene flanking PCR oligonucleotide (primer) used to amplify the mt1, ppk, and lacZ genes.

Another element of the plasmid that may be used for appropriate bioremediation strategies consists of a gene sequence coding for a protein which is, itself, a chelator or an enzyme capable of creating a sequestering molecule. Both/either the chelator protein and the enzyme capable of creating a sequestering molecule are referred herein to as a "chelator agent" or a "sequestration agent," interchangeably. In other words, any gene product which directly is a chelator or which creates a chelating or sequestering molecule are chelator agents in accordance to the invention. Examples of some chelator agents include ppk, mt1, phytochelatins, glutathione S transferase, and merP.

One preferred such chelator agent is a metallothionein (MT) protein. Metallothioneins (MT) are cysteine-rich low molecular weight metal-binding peptides that sequester metal ions in a biologically inactive form. Hamer, D. H., Annu. Rev. Biochem. 55:913-51 (1986). One particularly preferred mt gene is derived from mice ("the mt1 gene") and encodes the mt1 protein. The pCMV-SPORT 10 vector containing the mouse mt1 cDNA was obtained from the American Type Culture Collection (ATCC) clone #MGC47147. See also Strausberg, R. L. et al., *Proc Natl Acad Sci USA* 99:16899-16903 (2002). The mt1 gene was amplified by polymerase chain reaction (PCR) from the plasmid pCMV-SPORT 10 that contains the cDNA for the mt1 gene. The National Center for Biotechnology Information sequence for the mt1 coding sequence, gi #: BC036990, was used to design and develop PCR amplification primers that were used to isolate the mt1 coding sequence by PCR for subsequent cloning.

Another preferred chelator agent gene sequence is a ppk sequence that codes for polyphosphate kinase enzyme, which is responsible for the synthesis of strongly chelating polyphosphates. Inorganic polyphosphates are negatively charged long linear polymer chains of orthophosphates linked by high-energy phosphoanhydride bonds. Kornberg, A., J. Bacteriol. 177:491-496 (1995). These phosphate polymers can vary in length and are ubiquitous to all living organisms. The enzyme polyphosphate kinase encoded by the ppk gene undertakes the polymerization of gamma phosphates from ATP to form the long polyphosphate chains. A preferred ppk gene is derived from a bacterium, especially from an *E. coli*, and preferred ppk chelator agents are the polyphosphate kinase enzyme expressed from this gene and the polyphosphate products of this polyphosphate kinase enzyme. In a preferred embodiment, the ppk gene was amplified by PCR from *E. coli* K12 using PCR amplification primers designed off the NCBI sequence NC 000913. (The ppk gene is the 2.07 kb region from base 2,621,066 to 2,623,132 on the above NCBI sequence.) Akiyama, M. et al., *J. Biol. Chem.* 267: 22556-22561 (1992) and Blattner, F. R. et al., *Science.* 277: 1453-1474 (1997).

Yet another preferred chelator agent gene sequence is the lacZ gene sequence for β-galactosidase, derived from *E. coli* K12. The 3,072 base pair lacZ gene of K12 is part of the lactose operon in *E. coli* and expresses the enzyme β-galactosidase, which catalyzes the hydrolysis of disaccharides such as lactose. Kalnins, A. et al., *EMBO* 2:593-597 (1983). The *E. coli* β-galactosidase is a 464 kDa tetrameric protein that can be activated by potassium and magnesium ions as co-factors. This enzyme has been widely used in molecular biology and genetics because of its ability to metabolize X-Gal, a colorless modified galactose sugar that is metabolized to form an insoluble product (5-bromo-4 chloroindole) which is bright blue and can function as an indicator or reporter marker. The lacZ gene was amplified by PCR from *E. coli* K12 genomic DNA using PCR amplification primers designed off the NCBI sequence NC_000913. (The lacZ is the 3.08 kb region from base 362,455 to 365,529.) Blattner, F. R. et al., *Science.* 277:1453-1474 (1997).

It should be noted that in respect to mercury sequestration, the invention generally refers herein and exemplifies sequestration of inorganic mercury unless specifically discussed otherwise. However, the invention allows also for organic mercury sequestration if the system includes also a functional transgenic lyase, such as, for example, the merB gene. Ruiz, O. et al., Plant Physiol. 132:1344-1352 (2003); Bizily S., Proc Natl Acad Sci USA 96:6808-6813 (1999).

Another optional element of the expression cassette presented in one embodiment of the invention consists of a transcription termination sequence. In one preferred embodiment, the transcription termination sequence is a 3'UTR rho-independent transcriptional terminator sequence. Examples of preferred 3'-UTR sequences include bacterial and the plastid-derived rps16. Description for the bacterial rrnB terminator sequence is provided by Abe, H. et al., Genes to Cells, 4:87-97 (1999). A particularly preferred terminator is the plastid-derived rps16 terminator described by Hayes, M. L., et al., *Nucleic Acids Res.* 34:3742-3754 (2006) (herein-elsewhere also referred to as the rpsT) where "T" stands for "terminal." The rps16 gene transcriptional terminator sequence was integrated as a part of the synthetic 3' PCR amplification oligonucleotide (primer) for the mt1, ppk, and lacZ genes.

A convenient approach to the creation of cassettes comprising these genetic elements is to create synthetic oligonucleotides which are PCR primers for the transgene, where the two PCR primers comprise the 5' control elements (promoter, enhancer) and the 3'-UTR, respectively. Albeit hereinabove we described the particular molecular method (PCR, synthetic oligonucleotides, etc.) employed to obtain and prepare to transfer particular genetic elements into an expression cassette, it will be recognized by an artisan skilled in the art that alternative primers, alternative designs, and additional methodologies are available to accomplish the same goal of creating an expression cassette and a transfer vector comprising these genetic elements.

An expression cassette was constructed, comprising functionally connected: a transgene for expression and gene expression control elements. Listed above are preferred elements: the promoter derived from the plastid 16S rrn gene; the 5'UTR derived from bacteriophage T7 gene 10; and either the rrnB sequence or the rps16 transcriptional terminator (3'-UTR), preferably rps16. (Note that rps16 and rpsT are names used interchangeably for the same 3'-UTR in this patent specification.) This cassette comprises an unexpected combination of regulatory elements for usage in bacteria, which, have now been demonstrated, as further detailed below, to provide strong expression in bacteria. In accordance to one embodiment, the expression control sequences in the vector of the invention comprise strong promoter and 5' UTR, preferably the 16S rrn promoter sequence and the Bacteriophage T7 gene 10 5'UTR. In a more preferred embodiment, the vector further comprises a 3'UTR, preferably the rrnB or rps16 3'UTR, yet more preferably, the rps16 3'UTR. In accordance to preferred embodiments, the bacteria was engineered to express highly these chelator agent transgenic sequences. The resultant bacteria are resistant to high levels of heavy metal contamination.

As a corollary, the combination of preferred promoter, 5'UTR and 3'UTRs described here comprise a preferred expression system for high level expression of stable transcripts and translation products, whether the transgene expressed is a chelator agent or some other gene product.

The transformation methods for introducing vectors into the various cells and organisms are well known. For example, a vector construct may be introduced via calcium chloride/heat-shock method (chemically competent cells method), electroporation, via plasmid conjugation, particle bombardment and so on.

The vector is transformed into an organism in order to express a chelating agent. In a preferred embodiment, the vector is transformed into an organism that may be utilized for bioremediation, such as a plant, a fungus, an algae, or a bacterium.

In a particularly preferred embodiment, the organism is a bacterium. A preferred bacterium is an environmentally ubiquitous, non-finicky growing, easily sustainable in a natural environment bacterium. Particularly preferred bacteria for transformation with the expression cassettes and/or the transgene(s) encoding the sequestration agent(s) of the invention are *E. coli, Pseudomonas* sp (e.g. *Pseudomonas aeuriginosa*), *Cyanobacteria* sp (e.g. *Nostoc commune* or *Oscillatoria amoena*) and *Bacillus* sp (e.g. *Bacillus cereus*).

In preferred embodiments of the present invention, the chelator agent gene sequence is lacZ, mt1 or ppk. The transgenic bacteria expressing β-galactosidase, metallothionein and polyphosphate kinase were shown capable of removing heavy metals and mercury from liquids. The bacterial constructs described above have shown significant improvement in mercury resistance and accumulation to levels at least 8-fold higher than previously reported.

β-galactosidase ("β-gal") is a tetra peptide enzyme required in bacteria for lactose metabolism. β-gal has been well known since its protein sequence was unveiled in 1970. β-gal protein was not known to sequester heavy metals or mercury. As described in the examples below, β-gal has now been shown to have a high affinity for mercury and to bind mercury efficiently when over-expressed. It was not known that β-gal can confer resistance to bacteria exposed to large concentrations of mercury. Also β-gal protected against the harmful effects of high concentrations of cadmium, zinc, and lead.

When the β-galactosidase expression cassette (pBSK-P16S-g10-Bgal-rpst) was introduced in bacteria, a high level of transcription was observed. Furthermore, the bacteria became resistant to high concentrations of mercury. While the untransformed bacteria showed significant growth reduction upon exposure to 5 μg/ml Hg and did not grow at all at higher concentrations, bacteria transformed with the plasmid expressing β-gal are resistant to each of the tested concentrations of 0, 5, 10, 20, 40, 80, 100, 120, 140 and 160 μM mercury. The data presented in FIGS. 1 and 2 indicate the transformed bacteria not only survives mercury concentration of up to about 140 μM, but actually propagates at these levels of mercury. Other data (not shown in FIGS. 1 and 2) showed propagation of the transformed bacteria also at 160 μM Hg. Bacteria containing the plasmid easily tolerate, grow and replicate in like-concentrations of mercury found in polluted water and soil.

Figure 10A:
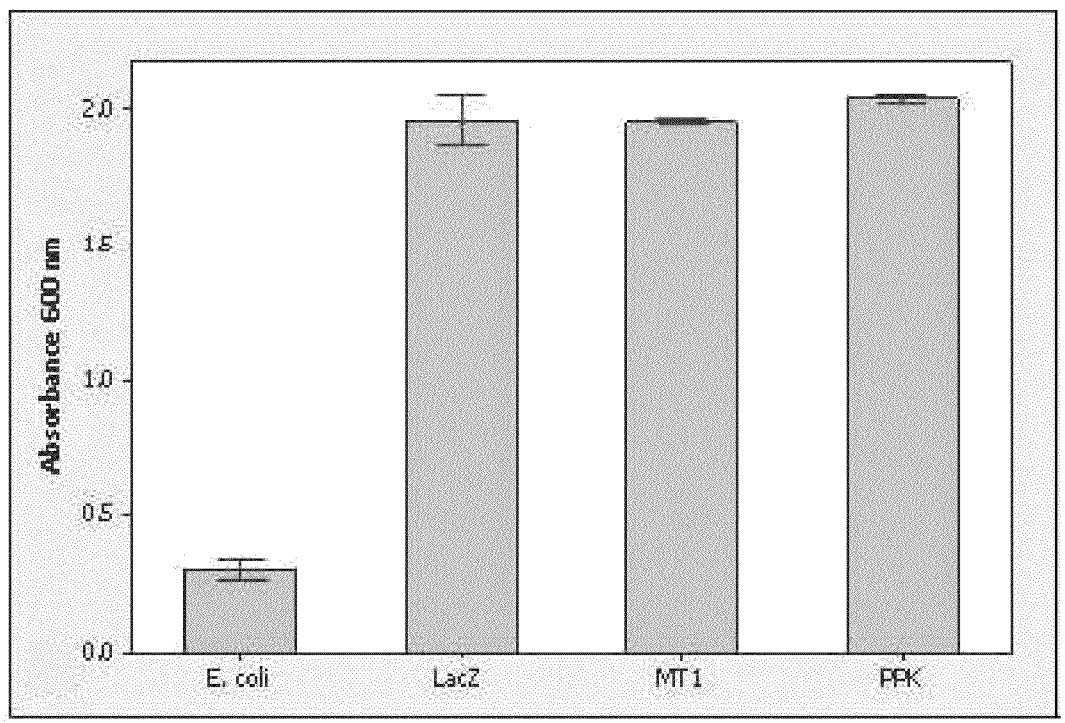
FIG. 10A shows the bacterial cell lines growing in 1,000 μM of $ZnCl_2$.
Figure 10B:
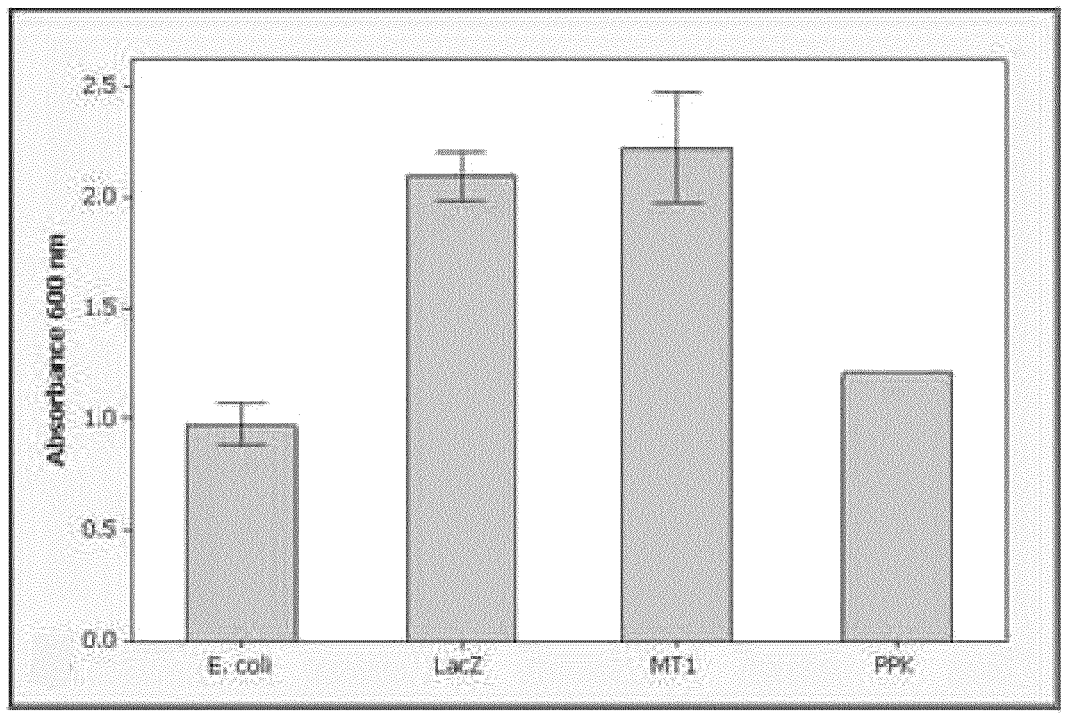
FIG. 10B shows the bacterial lines growing in 250 μM $CdCl_2$.
Figure 10C:
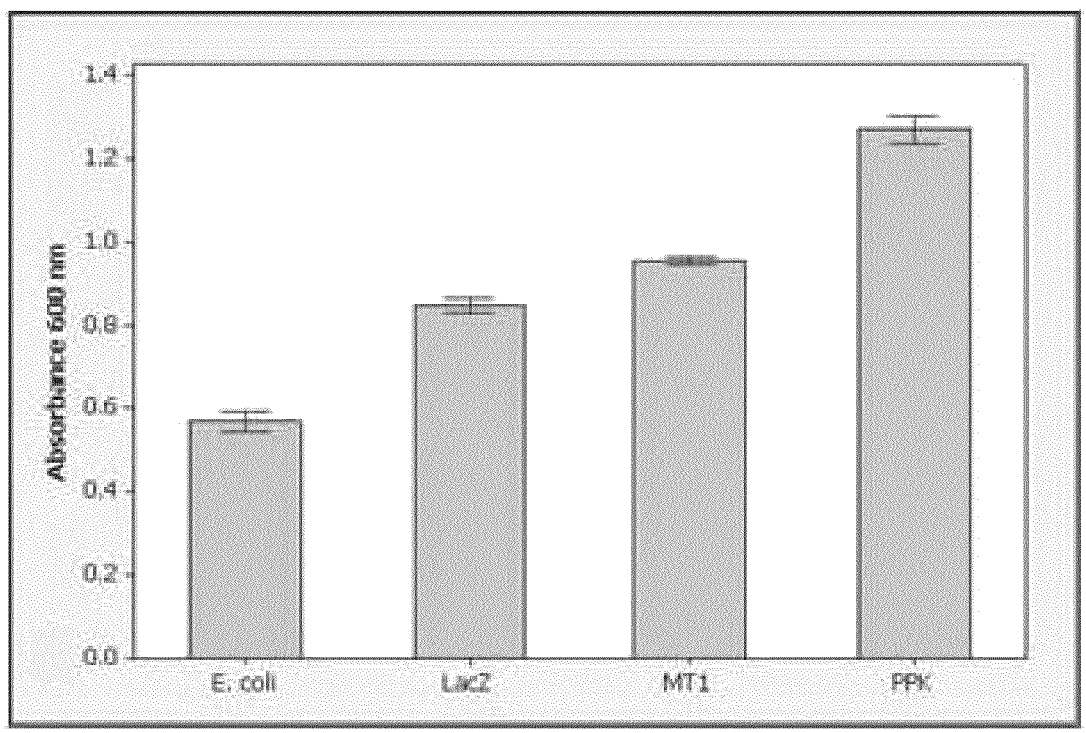
FIG. 10C shows the bacterial clones growing in 3,000 μM of lead acetate $Pb(C_2H_3O_2)_2 \cdot 3H_2O$.

Similar experiments, demonstrated that bacteria, when transformed with β-gal in accordance to the invention, can resist, and replicate in media containing up to at least about 250 μM cadmium (See FIG. 10). Also, the bacteria transformed with β-gal in accordance to the invention was able to resist and efficiently replicate in media containing up to at least about 1,000 μM zinc. This same transgenic bacteria demonstrated resistance up to at least about 3,000 μM lead.

When the mt1 expression cassette (pBSK-P16S-g10-mt1-rpst) was introduced in a bacterium, a high level of transcription was observed. See FIG. 3A. Furthermore, the bacteria became resistant to high concentrations of mercury. Bacteria transformed with the plasmid expressing mt1 were resistant to concentrations of mercury of 20, 40, 60, 80, 100, 120, 140 and 160 μM mercury. The data presented in FIGS. 1 and 2 indicate that the transformed bacteria not only survives mercury concentration of up to at least about 160 μM, but actually propagate at these levels of mercury. It should be noted that the bacterial growth rate is somewhat reduced, proportionally to the mercury level. Nonetheless, saturation levels of bacterial growth are achieved. Bacteria containing the plasmid easily tolerate, grow and replicate in like concentrations of mercury found in polluted water and soil.

Similar experiments, demonstrated that the bacterial clone expressing mt1 in accordance to the invention can resist and replicate in media containing up to at least about 250 μM cadmium, and up to at least 1000 μM zinc. The bacterial clones expressing mt1 also presented resistance to up to at least about 3,000 μM lead. See FIG. 10.

Similarly, when the ppk expression cassette was introduced in a bacterium, a high level of transcription was observed. See FIG. 3B. Furthermore, the bacteria became resistant to high concentrations of mercury. Bacteria transformed with the plasmid described above expressing mt1 were resistant to 20, 40, 60, 80 and 100 μM mercury. The data presented in FIGS. 1 and 2 indicate the transformed bacteria not only survives mercury concentration of up to about 100 μM, but actually propagate at these level of mercury. Bacteria containing the plasmid easily tolerate, grow and replicate in like concentrations of mercury found in polluted water and soil.

Similar experiments demonstrated that the bacterial clone expressing ppk in accordance to the invention can resist and replicate in media containing up to about 3,000 μM lead and 1,000 μM zinc. Additionally, the transgenic bacteria resisted cadmium up to about 250 μM. See FIG. 10.

Clearly, the vectors comprising the plastid 16S rrn-derived promoter, the T7 gene 10-derived 5'UTR and the bacterial-derived rrnB or the plastid-derived rps16 3'UTR are expressing these illustrated chelator genes in high copy numbers. As a corollary, these expression control sequences in combination can be used to express other genes at a high level, with similar copy numbers as seen for the chelator genes, or at least about 4,000; 4,500; 5,000; 5,500; 6,000; 6,500; 7,000; 7,500; 8,000; 8,500 full length copies per ng total mRNA.

Any genetic construct in a bacteria which comprises a strong promoter and/or appropriate 5'UTR and 3'UTR to cause production of at least about 4,000; 4,500; 5,000; 5,500; 6,000; 6,500; 7,000; 7,500; 8,000; 8,500 full length copies per ng total mRNA of a chelating agent mRNA in bacteria enables a bacteria comprising such construct to effectively remediate heavy metal containing liquids or solids, by chelating the heavy metal while resisting and propagating in an environment comprising the heavy metal. Preferably, the bacteria expresses about 6,000 to 7,500 copies of the chelator agent per ng total mRNA.

The transgenic bacteria having a plasmid comprising the β-galactosidase gene may be effectively used also as a biosensor for detection of mercury and mercury contamination and spills, and other heavy metals. The cleavage of X-gal releases 5,5'-dibromo-4,4'-dichloro-indigo, an insoluble blue compound. Transgenic bacteria expressing β-galactosidase in the presence of the compound X-Gal (and X-gal analogs) produces an easily distinguishable deep blue color reaction. However, it was now observed that the intensity of the blue color was reduced in proportion to the concentration of mercury. See FIG. 8 and FIG. 9. Similarly, the presence of other heavy metals, e.g. cadmium, could have the same effect of disrupting the cleavage of X-gal (and X-gal analogs) and production of the blue compound. These characteristic make β-gal suitable as a biosensor in situ or in vitro. Therefore, expression of β-galactosidase in bacteria protects the bacteria from the harmful effects of mercury, but also reduces the enzyme's ability to metabolize lactose and lactose-analogs, such as X-Gal.

In one aspect of the present invention, a kit for detection of heavy metals is presented. In accordance to one embodiment, the kit comprises a test vial or container for fluids, a bacterial culture expressing β-galactosidase or a β-galactosidase enzyme on a testing strip, 5-Bromo-4-chloro-3-indolyl-β-D-galactopyranoside (X-gal) and an indicator strip. The indicator strip contains color markers identifying the extent to which β-galactosidase reduces X-gal. Each marker may have a different shade of blue, such shade predetermined by exposure to different concentrations of the heavy metal, e.g. mercury.

The kit is utilized to implement a method of detecting mercury or other heavy metals including cadmium, lead and zinc. The method comprises the steps of placing a test sample in the container for fluids. Optionally, in case the test sample is a solid, liquid is added to release mercury/heavy metal from the solid. X-gal is added. The fluid is placed in contact with the bacterial culture or a testing strip comprising β-gal protein for a predetermined period of time. Next, the color of the culture is compared with the markers on the indicator strip to determine whether mercury is present in the fluid and in which concentration. In some cases of high heavy metal or mercury concentration, the kit may only provide a positive/negative result and not indicate a full range of concentrations.

An alternative embodiment of the kit described above may further comprise a set of standards. The standards may include various standard containers with various concentrations of Hg in solution. By way of a non-limiting example, the containers may have the following Hg concentrations A:0 μM; B:5 μM; C:10 μM; and D:20 μM.

The kit may be utilized in the following manner. A specified volume of test material and liquid (if the material is a solid) is placed in a test vial, a volume of Hg standard at the indicated concentrations is placed in each standard vial A:0 μM; B:5 μM; C:10 μM; and D:20 μM. A volume of transgenic bacteria is placed in each of the test and standard vials. X-gal is added to each vial. The culture is allowed to incubate for a specified period of time. Preferably the time of incubation is between about 1 minute and 20 minutes, more preferably between 5 and 10 minutes. After the incubation period ends, the coloring of the test vial is compared to the standard vials in order to determine the approximate concentration of mercury in the sample.

It will be well understood to an artisan skilled in the art that alternative embodiments are readily designed around the concept that mercury and other heavy metals progressively reduces β-gal's ability to cleave X-gal, in correlation to the concentration of the heavy metal. By way of examples, but not limited to these examples, the bacterium is provided in a non-liquid form (e.g., lyophilized), the bacterium comprising the β-gal is an environmental strain of bacteria, the incubation take place at a particular temperature, for example at 37° C. or at room temperature, purified β-gal is employed instead of a bacterium expressing the β-gal gene, or a β-gal expression vector or β-gal enzyme in the culture mix increases the range where the colored assay can correlate with concentrations of mercury. The test sample is a solid or a liquid wash of a solid. Likewise, alternative color assays and/or, the use of optical instruments (e.g., spectrophotometers, colorimeters) to precisely measure color change is possible. The use of color effect enhancing techniques are also known and possible. These alternative designs and others are well known to an artisan skilled in the art and are within the scope of the present invention.

In yet another aspect of the present invention, the β-galactosidase protein, itself, i.e., absent a cellular carrier, may be used as a chelating agent for heavy metals or mercury as part of a spill cleanup system for in situ and in vitro applications. β-gal is available commercially and can easily be purified from organisms expressing the enzyme by well known, standard separation techniques. The isolation of large quantities of the enzyme may be facilitated by its over expression and the commercial availability of antibodies to the enzyme. For manufacturing purposes, β-gal's expression in cells can be manipulated/increased by addition of IPTG. Commercial suppliers of β-gal protein are known, e.g., Sigma-Aldrich.

Similarly, metallothionein and the polyphosphate products of polyphosphate kinase may be utilized by themselves, i.e., absent a cellular carrier, as chelating agents for heavy metals including zinc, cadmium, lead, or mercury in remediation efforts.

Also, it has been shown in the present invention that a strong promoter, or specific 5'UTR and 3'UTR, or preferably, the specific combination of a strong plastid promoter, a bacteriophage T7 enhancer, and an effective plastid derived transcriptional terminator sequences allow the expression of metallothionein (mt1 gene), polyphosphate kinase (ppk gene), and β-galactosidase (lacZ gene) in bacteria to levels that permit their use and commercialization as an effective bioremediation system for mercury and other metals. The plasmid described above provides an enhanced gene expression construct capable of producing high mRNA transcription and protein translation of these and other transgenes.

The bacteria comprising the sequestering agents of the invention acquired properties that make them ideally suited for bioremediation by sequestration. For one, they were resistant to high levels of mercury for prolonged periods of time. See FIGS. 1 and 2. Not only they were resistant to high levels of mercury, but also they propagated at these levels. In controlled experiments, untransformed bacteria displayed reduced growth in the presence of 5 μM mercury, and no growth at 10 μM mercury. By contrast, the bacteria transformed with constructs expressing the pkk genes showed little or no reduction in growth in media containing 10 μM mercury and grew at concentrations of up to about 100 μM mercury. Significantly, the bacterial propagation continued over time. When the same constructs were tested after 120 hrs of growth in mercury, the lacZ construct showed further growth over time in up to about 140 μM mercury, undistinguishable in total growth level to untransformed bacteria grown without mercury. The mt1 construct showed further growth at up to 160 μM mercury (albeit at a somewhat reduced growth rate), undistinguishable in total growth level of the transformed or untransformed bacteria grown without mercury, and reduced but significant growth in media containing up to 160 μM mercury. The ppk construct showed further growth at up to 80 μM mercury, undistinguishable in total growth level of the transformed bacteria grown without mercury. The ppk construct showed a small reduction in growth at any concentration of mercury, from 0-80 μM. It is possible that phosphate availability had a small impact on the growth of bacteria transformed with the ppk gene.

The successful remediation of the fluid was shown in experiments where liquids containing 120 μM mercury were treated by exposure to the bacteria comprising the sequestration agents of the invention. See FIG. 7. After 120 hrs of treatment of the mercury containing media by exposure to the transgenic bacteria, the media was cleaned of remaining bacteria (resulting in "Treated Media"). An untransformed ("wt") bacterial seed was added to the Treated Media, fresh media comprising 0 μM mercury and fresh media comprising 120 μM mercury. The bacteria grew equally well in the Treated Media and the fresh media without mercury. This indicates that the Treated Media had mercury concentrations below 5 μM. The transgenic bacteria not only grew at these high levels of mercury, but also sequestered and removed the heavy metal.

Quantitative data produced by atomic absorption spectrometry analysis showed the remediation efficiency of the transgenic bacteria. See FIG. 11. Atomic absorption spectrometry analysis showed very high level accumulation of mercury in the transgenic $E.\ coli$ bacteria that expressed the lacZ gene. LacZ-expressing $E.\ coli$ cells were grown in LB media with 120 μM Hg for 120 hours at 37° C. The method of preparing the cells and media for spectrometric analysis is essentially in accordance with the Environmental Protection Agency Method 3010A. Cells were centrifuged, washed in fresh media, re-suspended in a small volume of media, digested with 70% (v/v) nitric acid, 30% (v/v) hydrogen peroxide, and concentrated HCl at 95° C., brought up to a volume equal to the initial volume in which they were grown and then analyzed by atomic absorption spectrometry. The supernatant media obtained after the centrifugation of the bacterial cells was also analyzed after similar treatment. The results indicated that the transgenic bacteria were very efficient at removing mercury from the media and accumulating the mercury in high concentrations inside the bacterial cells. As observed, most of the toxic mercury was found in the transgenic bacteria while mercury in the media was removed to non-toxic concentrations lower than 5 μM. These results demonstrate that the transgenic lacZ $E.\ coli$ has the capability of bioremediating liquids that are highly contaminated with mercury by chelation, while growing optimally.

Figure 8:
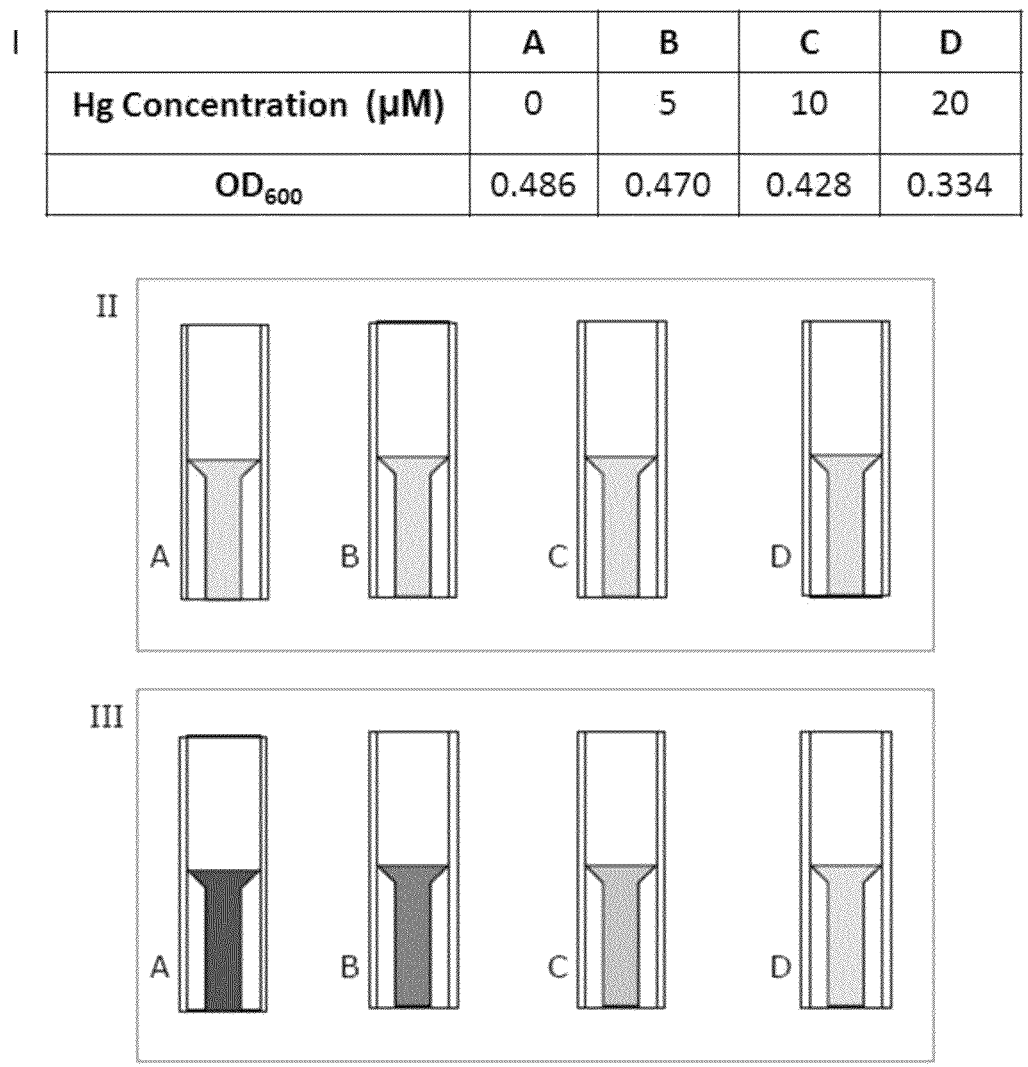
FIG. 8 illustrates the use of bacteria engineered in accordance to the invention to express the lacZ gene in order to determine the extent of heavy metal contamination of a liquid sample. For easier visualization, drawings were chosen to present the data captured in a Polaroid picture of the cuvettes. (The coloring is representative in its intensity to the coloring observed in the Polaroid picture for the cuvettes.) Cuvette A is growth in media containing 0 μM mercury; B is growth in media containing 5 μM mercury; C is growth in media containing 10 μM mercury; and D is growth in media containing 20 μM mercury. Panel I shows $OD_{600}$ measurements after 16 hours growth in the presence of the indicated levels of mercury. Panel II is a pictorial depiction of the measurements in Panel I. Panel III is bacteria as in the respective cuvettes of panel II, but where 100 μg/ml 5-Bromo-4-chloro-3-indolyl-β-D-galactopyranoside (X-gal) substrate per ml of media was added. The bacteria losses its ability to cleave X-gal and to produce the typical blue color, inversely proportional to the level of exposure to mercury.

Another very useful property was discovered in respect of the transformed bacteria, after exposure of these bacteria to heavy metal and to mercury, in particular. The bacteria, after sufficient accumulation of heavy metals including mercury, turned a darker shade. Furthermore, it tended to aggregate and clamp tightly. It is possible to scoop such aggregated bacteria from a container, aspirate in a manner such as pipetting the liquid, without necessitating specialized filters on which the bacteria can grow, or centrifugation. The aggregated bacteria were easy to visualize, as it changed coloration into a dark shade. See FIG. 6; FIG. 8, panel II; and FIG. 9, panel A.

The aggregation and dark shading properties can, individually or in combination, be put to good use in bioremediation. Accordingly, the present invention also provides a novel, simple, and low-cost mechanism for heavy metals or mercury bioremediation and uptake from liquids.

One method used in accordance with the present invention comprises a first step of placing the contaminated liquid in a reservoir. In a subsequent step, the bacteria comprising the plasmid expressing the sequestration/chelation agents of the present invention is added to the contaminated liquid. The bacteria are allowed to grow and remove the heavy metals from the liquid. As the bacteria remove mercury and reach a high concentration of mercury in the cells they precipitate from solution and form tightly bound aggregates. The aggregates are then recovered with a sifting device. Additional transgenic bacteria are added, as needed.

For another, the dark pigmentation is useful to indicate the process has progressed to the point where removal of the bacteria is required, or as a quality control that the process is actually under way, and the particular shading level can be utilized, by methods paralleling these described above for mercury monitoring with the lacZ system, to indicate or monitor the levels of mercury present in a contaminated environment.

Figure 4:
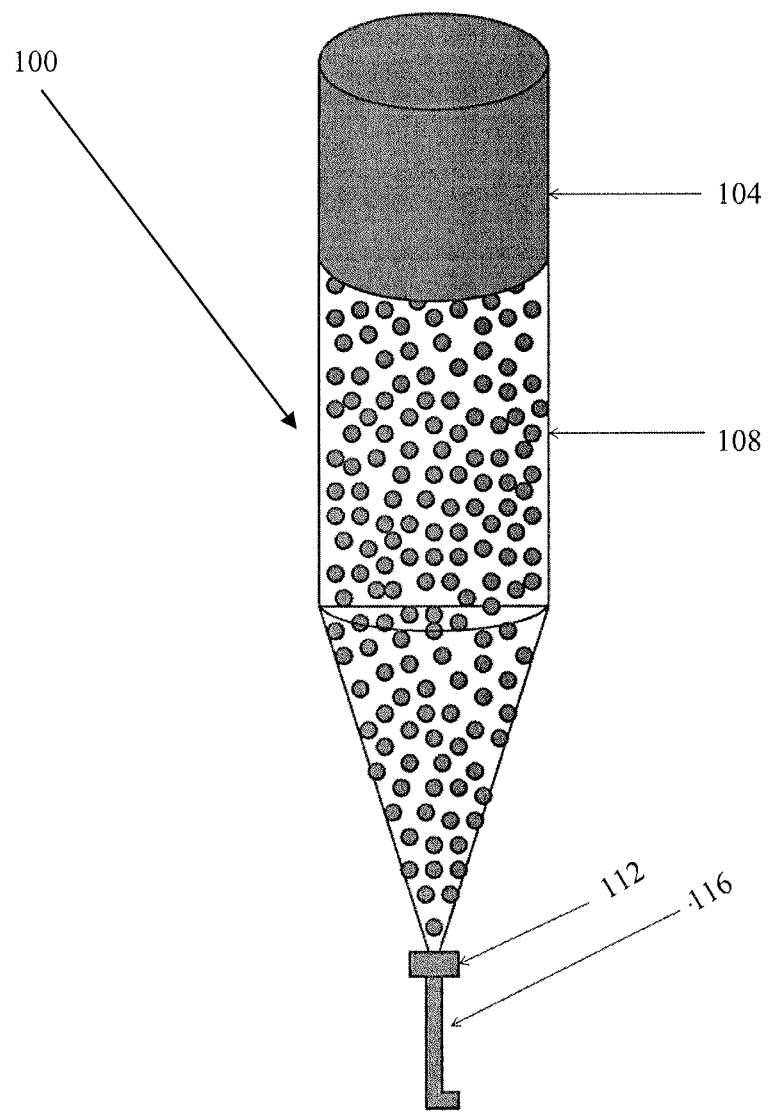
FIG. 4 is a graphic representation of an apparatus for bioremediation of contaminated liquids in accordance with one aspect of the present invention.

In another embodiment of the present invention, bacteria expressing the chelation agents in accordance to the invention form a self-sustained biofilm to use as part of filtration systems to remove heavy metals or mercury from liquid and solid matrices. In one preferred embodiment, as described in FIG. 4, a bioremediation system is provided comprising a water reservoir 104; a porous solid matrix 108; a cellular biofilm 100 in the water reservoir and/or in the porous solid matrix, wherein the Hg resistant bacteria comprising the genetic constructs of the invention make up the biofilm 100; a porous filter 112; and a treated water outlet 116. Genetically engineered bacteria may be grown onto the porous solid matrix 108 to form the biofilm 100.

Because the bacteria are highly resistant to mercury and other heavy metals, it efficiently removes mercury from the liquid while accumulating it in high concentrations inside the cells. High mercury tolerance also allows the bacterial cells to divide and grow, which prolongs the useful life of the biofilter. Coloring of the bacteria on the filter can indicate their bioremediation activity and when bacteria replacement is desirable.

In one method used in accordance with the present invention, contaminated water is loaded onto the water reservoir 104. The water is allowed to run through the porous solid matrix 208 and contact the cellular biofilm 100. The cells in the biofilm sequester heavy metal contaminants, such as mercury. The clean water passes through the porous filter 112 where any cellular matter dislodged from the biofilm 100 and other impurities are removed. Clean water is then released through the treated water outlet 116.

The combination of sequences described in this application may be used as a novel bioremediation system in various in-vitro systems, cell systems and organisms including bacteria, algae, plants, animals and fungi. The cell or organism may be genetically engineered to express the sequestering agents thereby becoming resistant to the heavy metals and cleaning the pollutant from the media by chelation. The organisms may be recovered and the heavy metal or mercury can be recovered and recycled for industrial applications. The in-vitro system, cell, or organism expressing or containing the proteins encoded by these sequences may also be used as part of a bioreactor or for in situ remediation of soil, water, and sediments.

In another embodiment in accordance with the present invention, a bacterial cell is provided comprising the heavy metal or mercury chelation system described above and a heavy metal/mercury transport mechanism. In one non-limiting example, a plasmid in accordance to the invention may also comprise the gene sequence for the merT and MerC gene of the mer operon. The plasmid may then be transformed into a bacterial cell conferring both the ability to transport mercury or other heavy metal into the cytoplasmic space and then sequester mercury within the cell. It is contemplated that other genes of the mer operon may also be utilized in order to enhance sequestration of heavy metals within the cell and to provide resistance to organomercurials such as methyl-mercury, dimethyl-mercury, and phenyl mercuric acetate. Alternatively, other heavy metal transport systems may be used in combination with the sequestration agents of the invention in a manner as described in the invention.

It is envisioned that bacterial or other organism systems comprising more than one gene encoding a sequestration agent may be created. This is made more facile by consideration that the cellular metabolic effects of the sequestration agents (other than sequestration) are different, and their activity as sequestering agents are also different (e.g. direct sequestration or the formation of polyphosphate molecules). Thus, the presence of more than one type of sequestration agent is expected to be relatively well tolerated by the host cell/organism.

EXAMPLE 1

Figure 5:
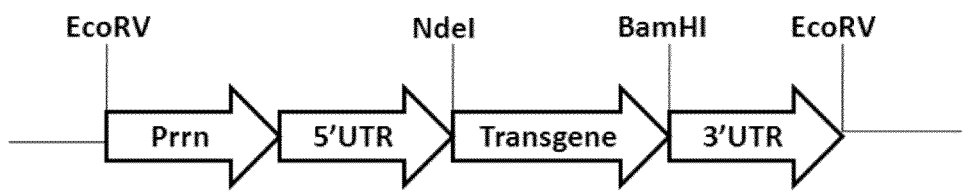
FIG. 5 is a schematic representation of a bacterial enhanced expression cassette. The restriction enzyme sites referred to in the figure represents only one embodiment of the invention. Prrn refers to a transcriptional promoter. In a preferred embodiment, the promoter is the plastid 16S rrn promoter. 5'UTR (untranslated region) represents a translational enhancer element. A preferred 5'UTR is from gene 10 of Bacteriophage T7. The transgene preferably encodes a sequestration agent. In a preferred embodiment, the sequestration agent is encoded by the lacZ, mt1, or ppk gene. 3'UTR refers to a transcription terminator. In a preferred embodiment, the transcription terminator is the plastid rps16 terminator or the $E.$ $coli$ rrnB terminator. In a particularly preferred embodiment, the transcriptional terminator is the rps16 terminator.
Figure 7A:
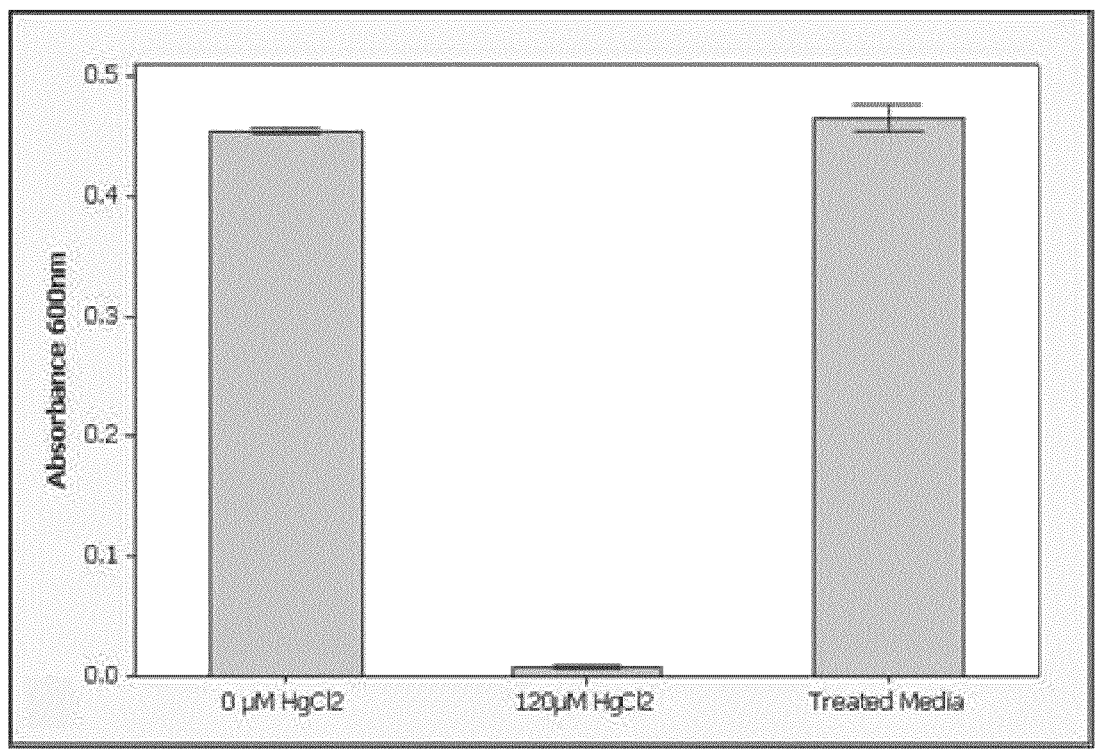
FIG. 7A shows growth for 24 hours of wt bacteria in media without mercury; media containing 120 μM mercury; and Treated Media. The Treated Media initially contained 120 μM mercury and was treated by exposure for 120 hours to bacteria engineered in accordance to the invention to express the lacZ gene, followed by removal of the bacterial cells.
Figure 7B:
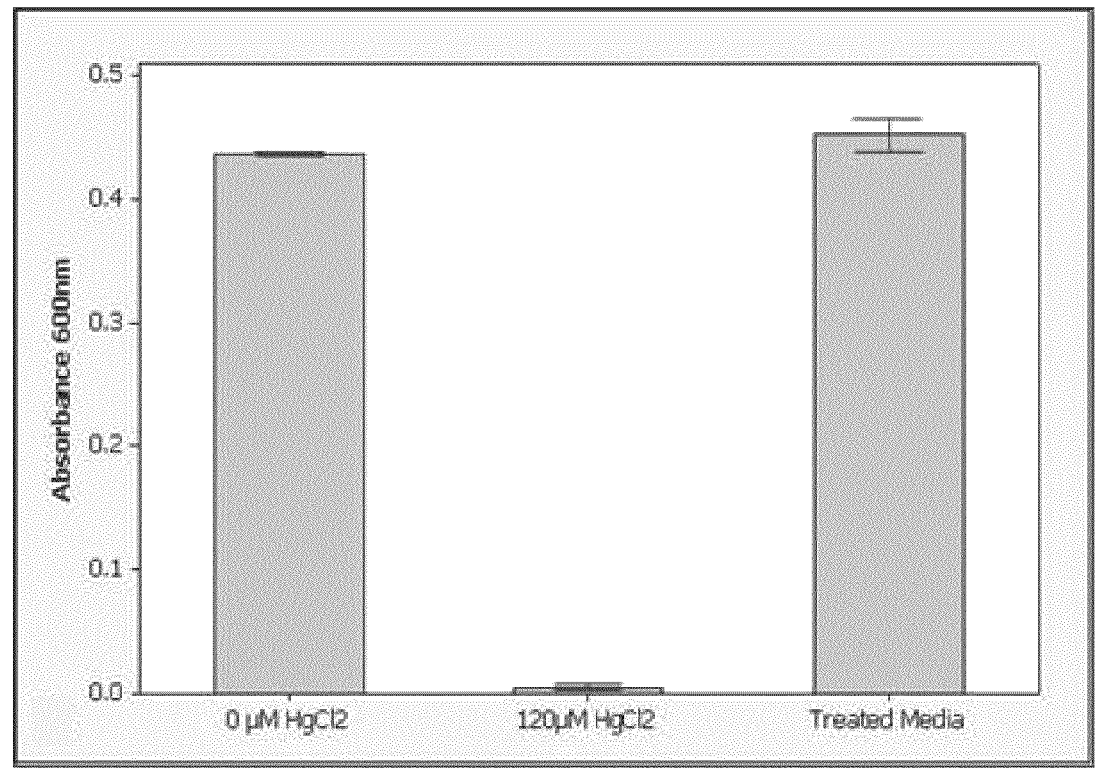
FIG. 7B shows growth for 24 hours of wt bacteria in media without mercury; media containing 120 μM mercury; and Treated Media. The Treated Media initially contained 120 μM mercury and was treated by exposure for 120 hours to bacteria engineered in accordance to the invention to express the mt1 gene, followed by removal of the bacterial cells.

The Sequestration Agents of the Invention Provide Tolerance to and Allow Bacterial Growth in the Presence of High Concentrations of Mercury, Cadmium, Zinc, and Lead In one embodiment of the present invention, a plasmid comprising a vector sold under the trademark pBlueScript® (Stratagene) was constructed to express transgenes at high level. The expression cassette in this vector comprised: the plastid 16S rrn gene promoter; the 5'UTR translational enhancer element is from bacteriophage T7 gene 10; the transgene; and the 3'UTR Rho-independent terminator as shown in FIG. 5. In one embodiment, the 3' UTR was the chloroplast rps16 sequence. The 5'UTR from Gene 10 was created from synthetic oligonucleotides. The other regulatory sequences were constructed via polymerase chain reaction. The genetic elements were created to comprise convenient restriction enzyme sites near the termini of each element. These methods are well known to artisans skilled in the art. See, for example, Sambrook, J., and Rusell, D., Molecular cloning: A laboratory manual. Cold Spring Harbor Lab press, Cold Spring Harbor, N.Y. (2001). Multiple plasmid constructs were created, where the transgene encoded lacZ, mt1, or ppk.

The bacterial clones containing these constructs were grown for 16 hours in LB media containing different concentration of $HgCl_2$, as shown in FIG. 1. In FIG. 1, FIG. 1A represents untransformed *E. coli* strain JM109, FIG. 1B represents transgenic *E. coli* comprising the pBSK-P16S-g10-lacZ-3'UTR vector, FIG. 1C represents transgenic *E. coli* comprising the pBSK-P16S-g10-mt1-3'UTR vector, and FIG. 1D represents transgenic *E. coli* clone carrying the pBSK-P16S-g10-ppk-3'UTR vector. A seed bacteria inoculum was added to bacterial culture flasks, and the flask was incubated with shaking at 37° C., in a typical fashion for growing bacterial cultures. At the end of the 16 hour incubation period, the absorbance of the culture media was measured at $OD_{600}$ nm.

Nearly identical constructs (but without the P16S promoter element) were also engineered and transformed into *E. coli*. In these P16 minus constructs, the promoter was off the vector, a lacZ promoter. The engineered bacteria comprising these P16S minus constructs also showed increased resistance and growth at high levels of mercury. For example, the mt1 gene construct survived up to about 20 μM Hg, and the ppk construct survived up to about 40 μM Hg. However, clearly, by comparison, the constructs that included the P16S element were able to survive significantly higher levels of mercury.

It appears that polyphosphate kinase provides better resistance to Hg than metallothionein when both proteins are expressed at lower levels, such as in the case of the pBSK-g10-mt1-rpsT and pBSK-g10-ppk-rpsT vectors. When these proteins are over-expressed, the metallothionein provided higher protection against the toxic effects of Hg than polyphosphate kinase. The invention is not limited by any mechanism of action of the specific chelator agents. Nonetheless, the difference in resistance to mercury in bacteria expressing ppk or mt1 at relatively lower or higher levels might be explained by the mechanism of action of the two proteins. In the case of metallothionein, because it directly sequesters Hg, higher expression levels equal higher resistance level. This differs from polyphosphate kinase, which can produce higher levels of polyphosphates even at lower enzyme concentrations because it is an enzyme. At higher enzyme concentrations, the increment in Hg resistance might be lower than expected because the availability of the enzyme substrate in the cell might be in a short supply, thereby limiting its activity. Polyphosphate kinase undertakes the polymerization of gamma phosphates from ATP to form the long polyphosphate chains.

The experimental results summarized in FIG. 1 show that *E. coli* untransformed with chelating agents ("wt") can grow in media containing up to about 5 μM Hg, although the growth is reduced upon exposure to 5 μM mercury. *E. coli* transformed with the indicated plasmid show growth in a 16 hours period when grown at concentrations of mercury ranging from 20 μM up to about: 40 (pkk); 80 (β-gal); 80 (mt1) μM mercury. In a similar experiment, as shown in FIG. 2, transgenic *E. coli* can continue to grow even in the presence of higher concentrations of mercury, and the cultures achieve higher densities after 120 hours incubation in LB media containing the various indicated concentrations of Hg, up to about mercury concentrations of: 100 μM for the ppk construct; 140 μM for the β-gal construct; and 160 μM for the mt1 construct. Accordingly, the bacteria resisted and continued growing at these high concentrations of mercury.

EXAMPLE 2

The Constructs of the Invention (pBSK-P16S-g10-Chelator Agent-3'UTR) Transcribed the Chelator Agent Element to Very High Levels mRNA was collected from untransformed bacteria and the mt1 and ppk expressing bacterial clones. The total cellular RNA was isolated by using the RNeasy Mini Kit (Qiagen) and protocol from 1 ml of bacterial clones and untransformed *E. coli* JM109 cultures grown in Luria Bertani (LB) broth for 16 hours at 37° C. with 300 rpm agitation. The RNA samples were treated with DNAse I at a concentration of 100 μg/ml.

The samples were normalized and reversed transcribed by random primer amplification using the AccuScript cDNA Kit (Stratagene). The cDNA was analyzed by quantitative real-time PCR using a two-step real-time PCR amplification program with post-amplification melt curve analysis. Gene-specific standard curves were produced for quantification from synthetic oligonucleotide. Real time PCR using transgene specific primers produced cDNA, in proportional amounts to the mRNA template. Control experiments using as template mRNA from untransformed bacteria showed no expression of the transgene. The copy number of the transgene specific mRNA was calculated and normalized to the total mRNA present. As can be see in FIG. 3, the clones contained about 7,000 copies of each of the transcripts per ng of total mRNA. Similar data is obtained with the construct comprising the B-gal element. An artisan skilled in the art will recognize that these numbers indicate the transgenes were transcribed to very high level.

EXAMPLE 3

Bacteria Containing the Sequestration Agents of the Invention Form Aggregates when they Accumulate Mercury Dark coloring, aggregation and precipitation were observed when the bacteria were grown in mercury at sufficiently high concentrations or at lower concentrations for sufficient lengths of time. For example, as shown in FIG. 6, pBSK-P165-g10 (5'UTR)-mt1-3'UTR ("mt1") and pBSK-P165-g10 (5'UTR)-lacZ-3'UTR ("lacZ") samples after incubation in LB media containing 120 μM Hg form aggregates that accumulate at the bottom of the container. Similar effects were also observed with transgenic bacteria comprising the mt1 or ppk genes grow in the presence of 80 μM mercury. The changes were observed after about 24 hours and they increased over time, proportional with accumulation. All the three bacterial clones were grown with agitation (at about 280 rpm) in a 15 ml conical tube. The aggregation and precipitation occurred during agitation, without the need for a stationary incubation. These color change and precipitation effects occur with each of the three chelator agents tested.

This provides a visual indicator of when the bacteria should be removed and replaced. This effect makes it easy to remove the bacteria that have accumulated large quantities of mercury by simply sifting it from the liquid.

These aggregation and precipitation effects have been observed in the bacterial clones pBSK-P16S-g10-mt1-rpsT and pBSK-P16S-g10-ppk-rpsT. Therefore it does not appear to be a direct function of the genotype, rather a function of resistance to and accumulation of mercury in the cell. The aggregation and precipitation was only observed in bacteria that had been growing in mercury concentrations equal or higher than 80 μM for a period of at least 24 hours. At lower mercury concentrations the cells would likely need to be exposed to mercury at low concentration for a longer period of time. Nonetheless, the color change, aggregation and precipitation occur also at lower concentrations of the mercury, once the bacteria have accumulated sufficient mercury.

The transgenic bacteria that accumulates mercury acquires a dark color, which serves as an indication of high mercury concentration in the cell. The darkening of the cells can be appreciated at 40 μM Hg or higher. The aggregation, precipitation, and coloring effects are very useful characteristics for identification and recovery of the bacterial cells once they accumulate high mercury concentrations; they can be useful markers to determine when a cell is ready to be harvested from the environment being cleaned, and can also help reduce the cost of applying these bacterial systems for mercury bioremediation. This is the first report of morphological changes triggered in bacterial cells due to the accumulation of mercury in high concentrations.

EXAMPLE 4

After Treatment of Culture Media by Exposure to Bacteria Comprising the Constructs of the Invention, the Treated Culture Media is Substantially Free of Heavy Metals; the Mercury was Sequestered As shown in FIG. 7, untransformed *E. coli* JM109 was cultured in LB media without mercury (0 µM), in Treated Media, and in LB media having a concentration of 120 µM $HgCl_2$.

Treated Media is LB media that initially contained 120 µM $HgCl_2$ and in which either bacterial clone pBSK-Prrn-5'UTR-lacZ-3'UTR or pBSK-Prrn-5'UTR-mt1-3'UTR were grown for 120 hours. Bacterial cells were removed from the liquid media by centrifugation at 13,000 rpm for 2 minutes and the liquid media was sterilized by passing it through a 0.22 µM filter to remove any transgenic bacterial cells left from the centrifugation process.

The Treated Media was re-inoculated with untransformed *E. coli* JM109. In the experiment shown in FIG. 7A, the Treated Media was media treated with bacteria comprising the pBSK-Prrn-5'UTR-lacZ-3'UTR ("lacZ") construct. In the experiment shown in FIG. 7B, the Treated Media was media treated with bacteria comprising the pBSK-Prrn-5'UTR-mt1-3'UTR ("mt1") construct. The untransformed bacteria were allowed to grow for 16 hours in the respective Treated Media, at 37° C. under standard bacterial culture conditions, and then the $OD_{600}$ absorbance of the culture was measured. Results show normal growth rate of the untransformed *E. coli* in the media that was treated by the transgenic bacteria. As a control, fresh media containing 120 µM Hg was also filter sterilized and *E. coli* JM109 bacteria was added. The untransformed JM109 bacteria were not capable of growing in media containing 120 µM $HgCl_2$. See FIGS. 7A and 7B. This indicates that transgenic clones of the invention can be used for remedial treatment of liquids containing very high concentrations of mercury. The treatment reduced Hg to non-toxic levels (less than about 5 µM) and allowed normal growth of *E. coli* JM109.

EXAMPLE 5

Figure 11:
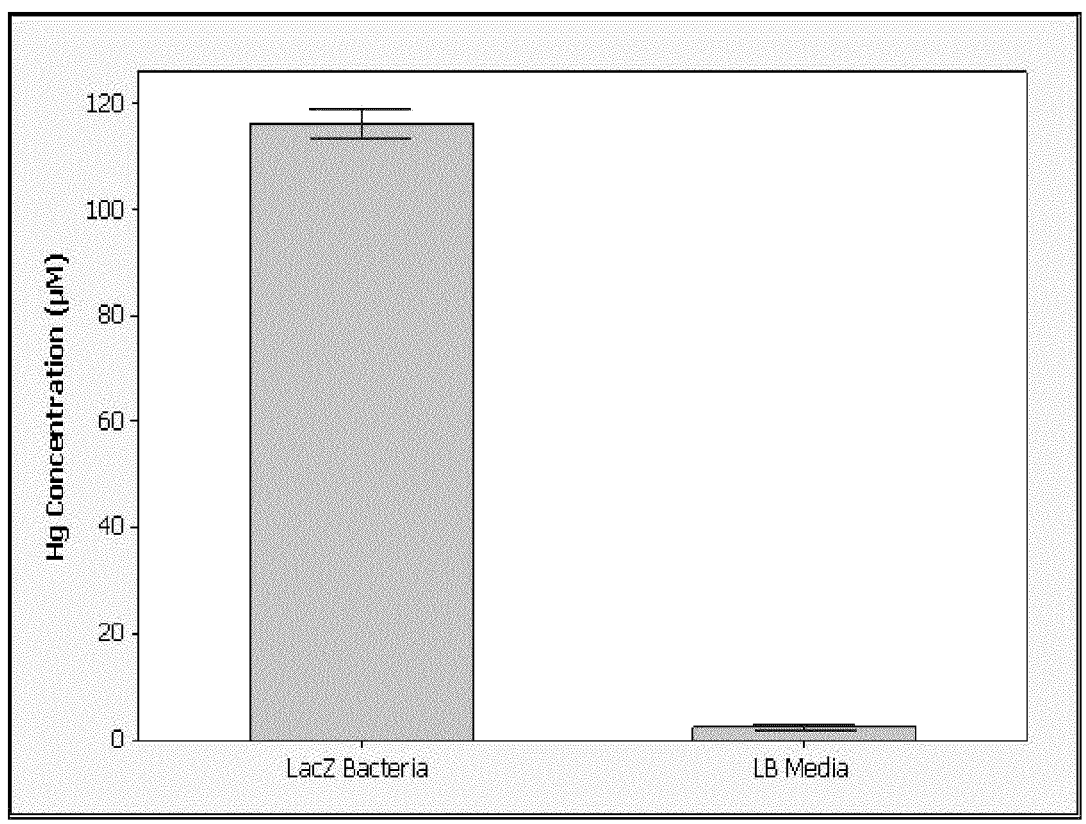
FIG. 11 shows sequestration of mercury by the bacteria expressing the transgenic genes. Bacteria transformed by a lacZ construct in accordance to the invention were grown for 120 hrs at 37° C. in media containing 120 μM mercury. The bacteria was removed by centrifugation, washed, and re-suspended in the same volume of media as the volume of the original culture. The re-suspended cells ("LacZ Bacteria") were treated to release any mercury and analyzed by atomic absorption spectrometry. The mercury concentration of the treated media and of the bacteria expressing the lacZ gene was calculated from the spectrometry results.

The Mercury is Sequestered within the Bacteria; the Transgenic Bacteria Reduces the Mercury to Sub-Bacterial Inhibitory Dosage To confirm that β-galactosidase can act as a chelator agent, we performed cold vapor atomic absorption spectrometry (CVAAS) analysis on pBSK-P16S-g10-lacZ-rpsT bacterial pellets obtained from 5 ml cultures in LB media with 120 µM Hg after 120 hours. The cells were removed from the culture by centrifugation, washed, and resuspended in 1 ml of LB media. The cells and the supernatant were acid-digested, individually, following EPA method 3010A (EPA Method 3010A. *Methods for Chemical Analysis of Water and Wastes*; U.S. Environmental Protection Agency: Washington, D.C., 1992), brought up to a 5 ml volume to maintain the initial Hg proportion, and then analyzed by CVAAS. The results indicated that the lacZ bacterial clone was very efficient at removing Hg from the media, accumulating a concentration equal to 116 µM of Hg (FIG. 11). The concentration left in the media after 120 hours of treatment was 2.7 µM (FIG. 11). These results validated the results that showed that untransformed *E. coli* grew exceedingly well in media previously treated with pBSK-P16S-g10-lacZ-rpsT bacterial clone. It was clear from both studies that the transgenic bacteria were capable of removing Hg from liquid cultures to levels lower than 5 µM.

EXAMPLE 6

β-Galactosidase Bioassay

Mercury Reduces β-Gal's Ability to Cleave X-Gal.

As shown in FIG. 8, a bacterial clone comprising the pBSK-P16S-g10-lacZ-rps16 plasmid was grown at the indicated concentrations of $Hg^{+2}$. Panel I shows the bacterial growth measurements ($OD_{600\ nm}$) after 16 hours in concentrations of $Hg^{+2}$ ranging from 0 to 20 µM $Hg^{+2}$. Duplicate cuvettes were then prepared for each bacteria grown at the indicated Hg concentration. See Panels II and III. 100 µg/ml X-gal was added to the cuvettes of Panel III. A reduction in the conversion of X-Gal to blue color was observed to be proportional to the increase in concentration of mercury, up to 20 µM $Hg^{+2}$. As observed in Panels I and II, bacterial growth of the transgenic clone was not affected by increasing concentrations of mercury within this range of concentrations. This indicates that the reduction in blue color is a factor of the reduction of β-gal enzymatic activity and not due to lack of bacterial growth.

For easier visualization, FIG. 8 presents drawings of the pictures of actual cuvettes containing samples in Panels II and III. The shading in the drawing are in accordance the shading of the pictures and the relative darkness of the cuvettes containing bacteria exposed to the different concentrations of Hg is preserved. Panel II is an exact drawing rendition of a picture of the cuvettes that shows bacterial growth after 16 hours in 0 to 20 µM $Hg^{+2}$. Panel III, is an exact drawing rendition of a picture of the cuvettes that shows that increased exposure and chelation of $Hg^{+2}$ by β-galactosidase reduces the enzyme's ability to convert X-gal substrate into a blue color metabolite. A:0 µM; B:5 µM; C:10 µM; D:20 µM. The shade for cuvette "D" in Panels II and III is visually identical.

Figure 9A:
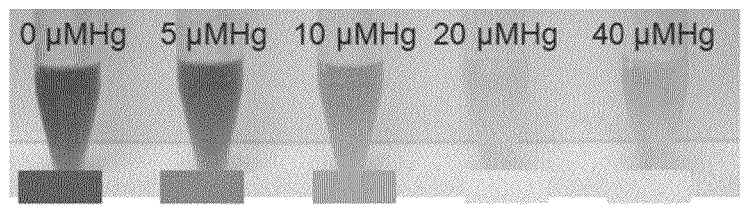
FIG. 9A is a photograph of the bacteria grown in the presence of the indicated amounts of mercury and 100 μg/ml X-gal. The colored bars underneath each culture vial approximates the color of the contents in the vial and are meant to be used as a color code to be supplied with a detection kit.
Figure 9B:
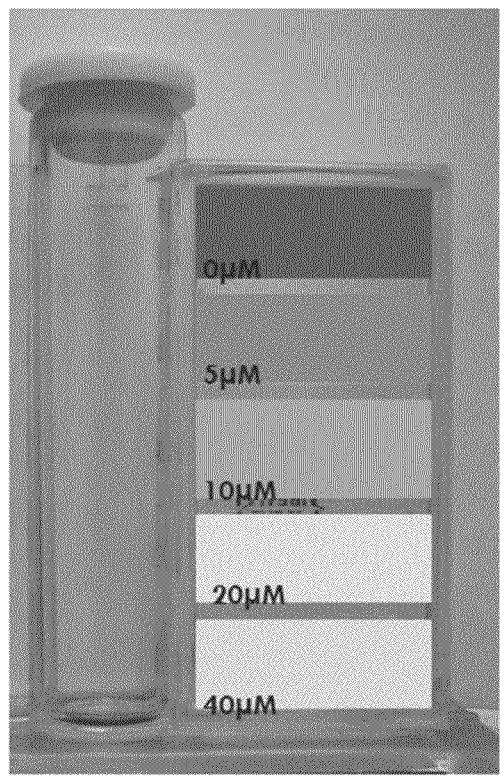
FIG. 9B depicts a tube for holding/growing a culture comprising bacteria expressing β-gal, X-gal and contaminated fluids. The container has attached thereto or comes accompanied by a color chart indicating expected color intensity for the bacterial culture in the presence of the indicated concentrations of mercury.
Figure 9C:
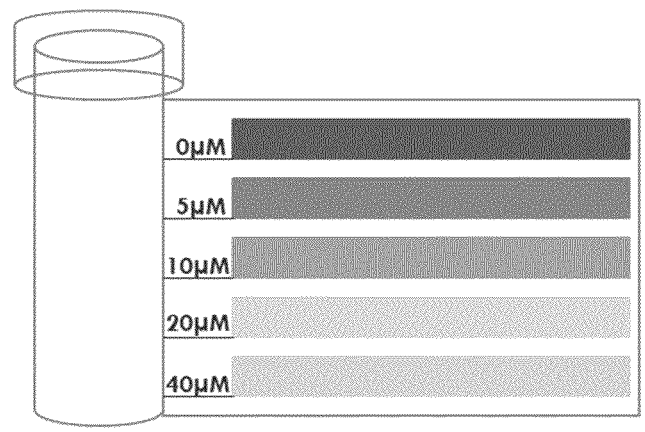
FIG. 9C is a schematic representation of FIG. 9B.

FIG. 9, Panel A shows actual photographs of similar experiments where the β-gal expressing bacterial clone was grown in the presence of 100 µg/ml X-gal and the indicated concentrations of mercury, for 16 hours at 37° C. As can be seen, the culture grown at 40 µM mercury starts developing a darker color. This darkening in color is the effect of accumulation in the cell of sequestered mercury. The colored bars at the bottom of each vial are color coding strips developed to mimic/capture the shade of the culture when exposed to the indicated concentrations of mercury.

FIG. 9, Panel B shows a prototype kit for detection of heavy metal contamination. A container is provided, where test liquids are added, as well as concentrated X-gal and a construct expressing β-gal or purified β-gal. Attached to the culture tube or in near proximity is a color code chart, to allow visual comparison of the test result to the color chart. Figure A is a schematic of the kit in FIG. 9B. After a period of incubation under standardized conditions, the color of the culture is compared to the color chart.

EXAMPLE 7

The Sequestration Agents Provide Resistance to Zinc, Cadmium, and Lead

Each of untransformed *E. Coli* JM109 ("wt") and bacterial culture expressing the lacZ, mt1, and ppk genes were seeded with bacteria at 0.01 $OD_{600}$ and were grown for 24 hrs in LB media supplemented with 1,000 µM $ZnCl_2$ (FIG. 10, Panel A); 250 µM $CdCl_2$ (Panel B); and 3,000 µM $Pb(C_2H_3)_2$ $2.3H_2O$ (Panel C). As can be seen in FIG. 10, the wt bacteria showed a certain level of resistance to these toxins. However, the transgenic bacteria was significantly more resistant. It is likely that these bacterial clones could continue to grow well in the presence of yet higher levels of zinc, cadmium and lead. There was only limited resistance shown by the ppk containing clone against cadmium. The clones showed reduced, but significant growth in the lead supplemented media. Growth of all three transformed bacteria in zinc and growth of the mt and β-gal clones in cadmium was essentially unimpeded. As a control, the wt and all three transformed bacterial strains grew equally well in the media not supplemented with a heavy metal (data not shown).

The invention described above should be read in conjunction with the accompanying claims and drawings. The description of embodiments and examples enable one to practice various implementations of the invention and they are not intended to limit the invention to the preferred embodiment, but to serve as a particular example of the invention. Those skilled in the art will appreciate that they may readily use the conception and specific embodiments disclosed as a basis for modifying or designing other methods and systems for carrying out the same purposes of the present invention.

All references, including publications, patent applications, patents, and website content cited herein are hereby incorporated by reference to the same extent as if each reference were individually and specifically indicated to be incorporated by reference and was set forth in its entirety herein.

The use of the terms "a" and "an" and "the" and similar referents in the context of describing the invention are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. A bacterium comprising a transgenic non-fusion mt1 chelator agent, wherein the bacterium is resistant to between at least 20 µM and about 160 µM Hg.

2. The bacterium of claim 1, which is resistant to between at least 20 gM and about 140 pM Hg.

3. The bacterium of claim 2, which is resistant to between at least 38 µM and about 140 µM Hg.

4. The bacterium of claim 2, which bacterium is not transgenic in respect to a mer operon functions affecting heavy metal transport to the cytoplasm.

5. The bacterium of claim 2, wherein the chelator agent gene is transcribed from a strong promoter and is flanked by a 5' UTR and a 3' UTR, whereby at least between 4,000 and 8,500 copies of stable transcripts per ng total mRNA correspond to the chelator gene.

6. The bacterium of claim 5, wherein at least between 6,000 and 7,500 copies of stable transcripts per ng total mRNA correspond to the chelator gene.

7. The bacterium of claim 5, wherein the chelator agent gene is flanked by a 5' UTR translational enhancer element sequence derived from bacteriophage T7 gene 10 and a plastid rps16 gene 3'UTR Rho-independent transcriptional terminator sequence.

8. The bacterium of claim 5, wherein the chelator agent gene is transcribed from a transcriptional constitutive promoter sequence derived from the plastid 16S rrn gene and is flanked by a 5' UTR transcriptional enhancer element sequence derived from bacteriophage T7 gene 10 and a plastid rps16 gene 3'UTR Rho-independent transcriptional terminator sequence.

9. The bacterium of claim 5, where the bacterium is resistant to above 20 µM up to about 140 µM mercury and cadmium at concentrations above about 200 µM up to about 250 µM, zinc at concentrations above about 500 µM up to about 1000 µM, or lead at concentrations above about 250 µM up to about 3,000 µM.

10. The bacterium of claim 2, which, when in a liquid environment containing mercury, accumulates the mercury and turns dark in coloring.

11. The bacterium of claim 2, which, when in a liquid environment containing mercury, cadmium, zinc or lead, accumulates the mercury, cadmium, zinc or lead and turns dark in coloring.

12. The bacterium of claim 1, selected from among *E. coli, Pseudomonas, Cyanobacteria* and *Bacillus*.

13. The bacterium of claim 1, which, when in a liquid environment containing mercury, cadmium, zinc or lead, it accumulates the mercury, cadmium, zinc or lead, forms aggregates and precipitates.

14. The bacterium of claim 1, grown in a biofilter for convenient handling to remove heavy metal from a contaminated liquid.

15. The bacterium of claim 1, wherein the chelator agent is not a fusion protein.

16. The bacterium of claim 4, wherein the chelator agent is not a fusion protein.

17. The bacterium of claim 1, wherein the chelator agent gene is transcribed from a strong promoter and is flanked by a 5' UTR and a 3' UTR, whereby at least between 4,000 and 8,500 copies of stable transcripts per ng total mRNA correspond to the chelator gene, and whereby the bacterium is resistant to between at least 20 µM and about 160 µM Hg.

18. A bacterium comprising a pBSK-P16S-g10-lacZ-3'UTR plasmid wherein the ability of β-galactosidase to cleave 5-Bromo-4-chloro-3-indolyl-β-D-galactopyranoside (X-gal) is reduced by the presence of mercury.

* * * * *